(12) United States Patent
Wang et al.

(10) Patent No.: US 11,155,537 B2
(45) Date of Patent: Oct. 26, 2021

(54) CRYSTAL OF BENZOFURAN DERIVATIVE FREE BASE AND PREPARATION METHOD

(71) Applicant: Jiangsu Hengrui Medicine Co., Ltd., Jiangsu (CN)

(72) Inventors: Likun Wang, Jiangsu (CN); Zhenxing Du, Jiangsu (CN); Qiyun Shao, Jiangsu (CN); Chao Xu, Jiangsu (CN)

(73) Assignee: Jiangsu Hengrui Medicine Co., Ltd., Jiangsu (CN)

(*) Notice: Subject to any disclaimer, the term of this patent is extended or adjusted under 35 U.S.C. 154(b) by 18 days.

(21) Appl. No.: 16/612,168

(22) PCT Filed: May 17, 2018

(86) PCT No.: PCT/CN2018/087272
§ 371 (c)(1),
(2) Date: Nov. 8, 2019

(87) PCT Pub. No.: WO2018/210302
PCT Pub. Date: Nov. 22, 2018

(65) Prior Publication Data
US 2021/0130333 A1    May 6, 2021

(30) Foreign Application Priority Data
May 18, 2017 (CN) .......................... 201710350574.5

(51) Int. Cl.
C07D 405/14 (2006.01)
A61K 31/4545 (2006.01)

(52) U.S. Cl.
CPC ........ *C07D 405/14* (2013.01); *A61K 31/4545* (2013.01)

(58) Field of Classification Search
None
See application file for complete search history.

(56) References Cited

U.S. PATENT DOCUMENTS 10,759,787 B2 * 9/2020 Lu ........................ A61P 35/00

FOREIGN PATENT DOCUMENTS

| CN | 103987842 A | 8/2014 |
|---|---|---|
| WO | 2011/140325 A1 | 11/2011 |
| WO | 2012/005805 A1 | 1/2012 |
| WO | 2012/050532 A1 | 4/2012 |
| WO | 2012/118812 A2 | 9/2012 |
| WO | 2012/142504 A1 | 10/2012 |
| WO | 2012/142513 A1 | 10/2012 |
| WO | 2013/039988 A1 | 3/2013 |
| WO | 2013/049770 A2 | 4/2013 |
| WO | 2013/067300 A1 | 5/2013 |
| WO | 2014/097041 A1 | 6/2014 |
| WO | 2015/141616 A1 | 9/2015 |
| WO | 2017/084494 A1 | 5/2017 |

OTHER PUBLICATIONS

Morissette et al, Advanced Drug Delivery Reviews, vol. 56, pp. 275-300 (Year: 2004).*
Schultz et al, "Asymmetric Synthesis of 1,6-Dialkyl-1,4-cyclohexadine Derivatives," Journal of the American Chemical Society, vol. 113, No. 13, pp. 4931-1936 (1991).
Int'l Search Report dated Aug. 14, 2018 in Int'l Application No. PCT/CN2018/087272.

* cited by examiner

*Primary Examiner* — Zinna Northington Davis
(74) *Attorney, Agent, or Firm* — Ice Miller LLP

(57) ABSTRACT

This application describes a crystal of a benzofuran derivative free base and a preparation method. Specifically, this application describes crystal A, crystal B, crystal C, and crystal D of N-((4,6-dimethyl-2-carbonyl-1,2-dihydropyridin-3-yl)methyl)-5-ethyl-6-(ethyl(tetrahydro-2H-pyran)4-yl)amino)-2-(piperidin-1-ylmethyl)benzofuran-4-carboxamide and a preparation method for the crystals. The crystals of the compound of formula (I) have great crystal stability and provides improved uses in clinical treatment.

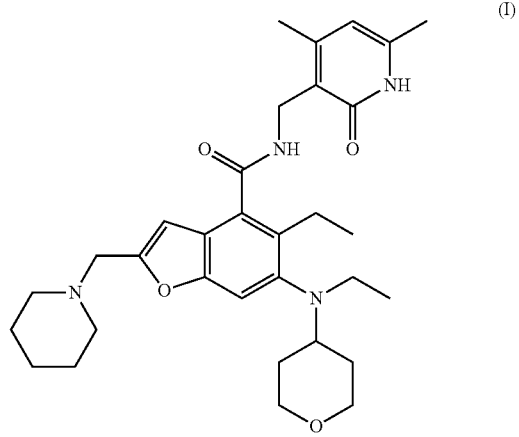

17 Claims, 17 Drawing Sheets

CRYSTAL OF BENZOFURAN DERIVATIVE FREE BASE AND PREPARATION METHOD

CROSS-REFERENCE TO RELATED APPLICATION

This application is a Section 371 of International Application No. PCT/CN2018/087272, filed May 17, 2018, which was published in the Chinese language on Nov. 22, 2018, under International Publication No. WO 2018/210302 A1, which claims priority under 35 U.S.C. § 119(b) to Chinese Application No. 201710350574.5, filed May 18, 2017, the disclosures of which are incorporated herein by reference in their entirety.

FIELD OF THE INVENTION

The present invention relates to crystal forms A, B, C and D of N-((4,6-dimethyl-2-oxo-1,2-dihydropyridin-3 -yl)methyl)-5-ethyl-6-(ethyl(tetrahydro-2 H-pyran-4-yl)amino)-2-(piperidin-1-ylmethyl)benzofuran-4-carboxamide, as well as preparation methods thereof.

BACKGROUND OF THE INVENTION

Lymphoma is a malignant tumor originating from the lymphoid hematopoietic system. It is classified into non-Hodgkin lymphoma (NHL) and Hodgkin lymphoma (HL) according to the tumor cells. In Asia, 90% of lymphoma patients are NHL patients having lymphocytes, histiocytes or reticular cells with different degrees of differentiation in pathology. According to the natural course of NHL, NHL can be classified into three major clinical types, namely highly invasive, invasive and indolent lymphoma. According to the different lymphocyte origins, it can be classified into B cells, T cells and natural killer (NK) cells lymphoma. The main function of B cells is to secrete various antibodies to protect the body against various external invasions.

The histone methyltransferase encoded by the EZH2 gene is a catalytic component of polycomb repressive complex 2 (PRC2). EZH2 levels are abnormally elevated in cancer tissues compared to normal tissues, and EZH2 is most highly expressed in advanced cancers or poor prognosis. In some types of cancers, EZH2 overexpression occurs simultaneously with amplification of the EZH2 gene. A number of si/shRNA experimental studies show that reduction of EZH2 expression in tumor cell lines can inhibit tumor cell proliferation, migration and invasion, or angiogenesis, and lead to apoptosis. WO2017084494 (PCT/CN2016/104318, filing date of 2 Nov. 2016) discloses an EZH2 inhibitor having the following structure:

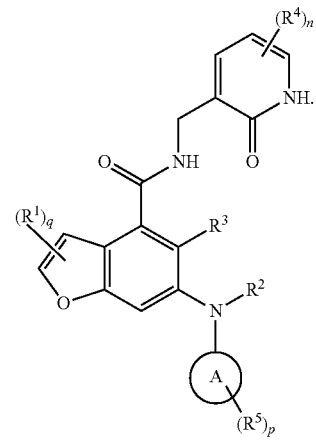

Patent application that discloses selective EZH2 inhibitor includes WO2012005805, WO2012050532, WO2012118812, WO2012142513, WO2012142504, WO2013049770, WO2013039988, WO2013067300, WO2015141616, WO2011140325 and the like.

The crystal structure of a pharmaceutically active ingredient often affects the chemical stability of the drug. Different crystallization conditions and storage conditions may lead to changes in the crystal structure of a compound, and sometimes accompanying production of other crystal forms. In general, an amorphous drug product does not have a regular crystal structure, and often has other defects such as poor product stability, excessively fine crystal, difficult filtration, easy agglomeration, and poor liquidity. The polymorphic forms of a drug have different requirements on storage, production and amplification. Therefore, it is necessary to investigate the crystal forms of the compound of formula (I) and the preparation method thereof so as to improve the various properties of the compound of formula (I).

SUMMARY OF THE INVENTION

The technical problem to be solved by the present invention is to provide crystal forms A, B, C and D of N-((4,6-dimethyl-2-oxo-1,2-dihydropyridin-3-yl)methyl)-5 -ethyl-6-(ethyl(tetrahydro-2 H-pyran-4-yl)amino)-2-(piperidin-1-ylmethyl)benzofuran-4-carboxamide, as well as preparation methods thereof. The crystal forms prepared by the present invention have a good stability.

The technical solution of the present invention is as follows:

The present invention provides crystal form A of a compound of formula (I), characterized in that: the crystal form A has a powder X-ray diffraction spectrum, which is obtained by using Cu-Kα radiation and represented by diffraction angle 2θ angle, in which there are characteristic peaks at diffraction angle 2θ angles of 7.60, 8.51, 11.80, 12.38, 13.52, 13.73, 14.48, 15.23, 15.99, 16.10, 16.82, 16.99, 17.35, 18.24, 20.82, 21.57, 21.91, 22.57, 22.76, 22.88, 24.29, 24.47, 25.24, 25.90, 27.23 and 27.74, wherein the error range of 2θ angle of each characteristic peak is±0.2,

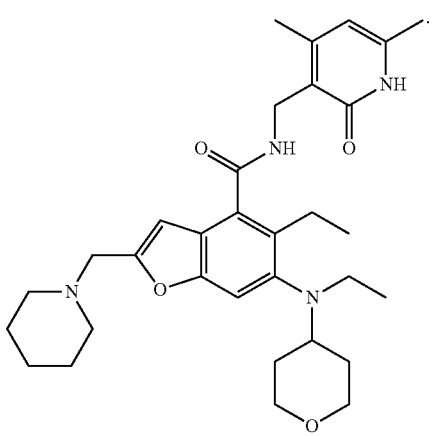

(I)

Preferably, there are characteristic peaks at diffraction angle 2θ angles of 7.60, 8.51, 10.37, 11.16, 11.80, 12.38, 12.89, 13.52, 13.73, 14.03, 14.48, 15.23, 15.99, 16.10, 16.43, 16.82, 16.99, 17.35, 18.24, 18.92, 19.17, 20.68, 20.82, 21.57, 21.91, 22.57, 22.76, 22.88, 23.53, 23.68, 24.00, 24.29, 24.47, 24.91, 25.24, 25.72, 25.90, 27.23, 27.74 and 35.63, wherein the error range of 2θ angle of each characteristic peak is ±0.2.

The present invention also provides the single crystal data of crystal form A, characterized in that the crystal form A is an orthorhombic crystal system; the space group is Pbca; the unit cell parameters are a=17.051(3)Å, b=15.840(3)Å, c=23.249(5)Å, α=β=γ=90.0; and the unit cell volume is 6279(2)Å$^3$.

The present invention also provides a method for preparing the crystal form A, characterized in that the method is selected from the group consisting of:

method I, dissolving the compound of formula (I) in a solvent to crystallize, filtering, washing and drying the resulting crystal to obtain the desired crystal form A, wherein the solvent is selected from the group consisting of an amide solvent, a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile, and the crystallization method is selected from the group consisting of room temperature crystallization, cooling crystallization, solvent volatilization crystallization and crystallization induced by addition of a seed crystal;

method II, dissolving the compound of formula (I) in a good solvent, adding an anti-solvent to crystallize, filtering and drying the resulting crystal to obtain the desired crystal form A, wherein the good solvent is an alcohol solvent, the alcohol solvent is selected from the group consisting of methanol, ethanol and isopropanol, and the anti-solvent is water, and the crystallization method is selected from the group consisting of room temperature crystallization, cooling crystallization, solvent volatilization crystallization and crystallization induced by addition of a seed crystal; and method III, adding the compound of formula (I) to a solvent, pulping the mixture, filtering and drying the resulting crystal to obtain the desired crystal form A, wherein the solvent is selected from the group consisting of a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile.

The present invention also provides a method for preparing the single crystal of crystal form A, characterized in that the method comprises:

dissolving the compound of formula (I) in a solvent to crystallize, filtering and drying the resulting crystal to obtain the desired single crystal of crystal form A, wherein the solvent is a mixed solvent of a halohydrocarbon and a nitrile, the halohydrocarbon solvent is dichloromethane, and the nitrile solvent is acetonitrile; the ratio of the halohydrocarbon to the nitrile is 20:1-1:20, and preferably 1:10, the crystallization method is selected from the group consisting of room temperature crystallization, cooling crystallization, solvent volatilization crystallization and crystallization induced by addition of a seed crystal.

The present invention also provides crystal form B of the compound of formula (I), characterized in that: the crystal form B has a powder X-ray diffraction spectrum, which is obtained by using Cu-Kα radiation and represented by diffraction angle 2θ angle, in which there are characteristic peaks at diffraction angle 2θ angles of 6.31, 7.24, 10.99, 12.07, 14.56, 17.94, 19.13, 19.71, 21.48, 24.15, 27.10 and 28.83, wherein the error range of 2θ angle of each characteristic peak is ±0.2.

Preferably, there are characteristic peaks at diffraction angle 2θ angles of 6.31, 7.24, 8.92, 10.38, 10.99, 12.07, 14.56, 15.10, 16.36, 17.29, 17.94, 19.13, 19.71, 21.12, 21.48, 22.59, 24.15, 25.45, 26.28, 26.52, 27.10, 28.83, 30.07, 31.37, 32.56, 33.65, 34.64, 36.09, 37.13 and 40.04, wherein the error range of 2θ angle of each characteristic peak is ±0.2.

The present invention also provides a method for preparing the crystal form B, characterized in that the method is selected from the group consisting of:

method I, dissolving the compound of formula (I) in a solvent to crystallize, filtering and drying the resulting crystal to obtain the desired crystal form B, wherein the solvent is ethanol, and the crystallization method is selected from the group consisting of room temperature crystallization, cooling crystallization, solvent volatilization crystallization and crystallization induced by addition of a seed crystal; and method II, dissolving the compound of formula (I) in a good solvent, adding an anti-solvent to crystallize, filtering and drying the resulting crystal to obtain the desired crystal form B, wherein the good solvent is ethanol, and the anti-solvent is water, the crystallization method is selected from the group consisting of room temperature crystallization, cooling crystallization, solvent volatilization crystallization and crystallization induced by addition of a seed crystal.

The present invention further provides crystal form C of the compound of formula (I), characterized in that: the crystal form C has a powder X-ray diffraction spectrum, which is obtained by using Cu-Kα radiation and represented by diffraction angle 2θ angle, in which there are characteristic peaks at diffraction angle 2θ of 7.40, 8.62, 9.49, 12.32, 13.39, 15.52, 19.15, 19.17, 21.42 and 22.78, wherein the error range of 2θ angle of each characteristic peak is ±0.2.

Preferably, there are characteristic peaks at diffraction angle 2θ angles of 7.40, 8.62, 9.49, 9.96, 11.12, 12.32, 13.39, 14.21, 14.85, 15.52, 16.50, 17.67, 18.28, 19.15, 19.17, 20.06, 20.80, 21.42, 21.89, 22.20, 22.78, 23.41, 24.74, 25.34, 26.70, 27.38, 28.64, 29.63, 30.20 and 31.15, wherein the error range of 2θ angle of each characteristic peak is ±0.2.

The present invention also provides a method for preparing the crystal form C, characterized in that the method comprises the following steps of:

dissolving the compound of formula (I) in a good solvent, adding an anti-solvent to crystallize, filtering and drying the resulting crystal to obtain the desired crystal form C, wherein the good solvent is an ether solvent, the ether solvent is 1,4-dioxane, the anti-solvent is selected from the group consisting of an aliphatic hydrocarbon solvent and an alicyclic hydrocarbon solvent, the aliphatic hydrocarbon solvent is n-heptane, and the alicyclic hydrocarbon solvent is cyclohexane, and the crystallization method is selected from the group consisting of room temperature crystallization, cooling crystallization, solvent volatilization crystallization and crystallization induced by addition of a seed crystal.

The present invention also provides crystal form D of the compound of formula (I), characterized in that: the crystal form D has a powder X-ray diffraction spectrum, which is obtained by using Cu-Kα radiation and represented by diffraction angle 2θ angle, in which there are characteristic peaks at diffraction angle 2θ angles of 8.41, 8.85, 11.38, 12.18, 13.45, 15.15, 16.73, 17.59, 17.68, 20.45, 21.51, 22.72, 24.53, 24.91 and 27.11, wherein the error range of 2θ angle of each characteristic peak is ±0.2.

Preferably, there are characteristic peaks at diffraction angle 2θ angles of 8.41, 8.85, 10.15, 11.38, 12.18, 13.45, 14.40, 15.15, 16.73, 17.59, 17.68, 18.42, 18.91, 19.22, 20.45, 21.15, 21.51, 22.11, 22.72, 24.03, 24.53, 24.91, 25.54, 26.54, 27.11, 27.61, 29.04, 30.49, 31.31, 33.00, 33.88, 35.52, 37.53, 40.46, 41.36, 42.40 and 44.02, wherein the error range of 2θ angle of each characteristic peak is ±0.2.

The present invention also provides the single crystal data of crystal form D, characterized in that the crystal form D is an orthorhombic crystal system; the space group is Pbca; the unit cell parameters are a=17.4737(6)Å, b=17.5933(5)Å, c=19.9907(7)Å, α=β=γ=90.0°; and the unit cell volume is 6145.5 (3)Å$^3$.

The present invention also provides a method for preparing the crystal form D, characterized in that the method is selected from the group consisting of:

method I, dissolving the compound of formula (I) in a solvent to crystallize, filtering and drying the resulting crystal to obtain the desired crystal form D, wherein the solvent is selected from the group consisting of an alcohol solvent, an ether solvent, a mixed solvent of an alcohol and water, a mixed solvent of an ether and water, a mixed solvent of an alcohol and an aliphatic hydrocarbon, and a mixed solvent of an ether and an aliphatic hydrocarbon, the alcohol solvent is selected from the group consisting of methanol, ethanol and isopropanol, the ether solvent is selected from the group consisting of tetrahydrofuran and 1,4-dioxane, and the aliphatic hydrocarbon solvent is n-heptane, and the crystallization method is selected from the group consisting of room temperature crystallization, cooling crystallization, solvent volatilization crystallization and crystallization induced by addition of a seed crystal;

method II, dissolving the compound of formula (I) in a good solvent, adding an anti-solvent to crystallize, filtering and drying the resulting crystal to obtain the desired crystal form D, wherein the good solvent is selected from the group consisting of an alcohol solvent and an ether solvent, the alcohol solvent is selected from the group consisting of methanol and isopropanol, the ether solvent is tetrahydrofuran, and the anti-solvent is water; or the good solvent is an ether, the ether solvent is tetrahydrofuran, the anti-solvent is selected from the group consisting of an aliphatic hydrocarbon solvent and an alicyclic hydrocarbon solvent, the aliphatic hydrocarbon solvent is n-heptane, and the alicyclic hydrocarbon solvent is cyclohexane, and the crystallization method is selected from the group consisting of room temperature crystallization, cooling crystallization, solvent volatilization crystallization and crystallization induced by addition of a seed crystal; and method III, adding the compound of formula (I) to a solvent, pulping the mixture, filtering and drying the resulting crystal to obtain the desired crystal form D, wherein the solvent is selected from the group consisting of water, an ester, an ether, an aliphatic hydrocarbon, an alicyclic hydrocarbon, a nitroalkane solvent, an arene, an alcohol, a nitrile, a halohydrocarbon, a ketone, a sulfoxide, an amide, a mixed solvent of an alcohol and an ether, a mixed solvent of an alcohol and water, and a mixed solvent of one or more alcohol, the ester solvent is selected from the group consisting of ethyl acetate, isopropyl acetate and butyl acetate, the ether solvent is selected from the group consisting of tetrahydrofuran, 1,4-dioxane, propylene glycol methyl ether and methyl tert-butyl ether, the aliphatic hydrocarbon is n-heptane, the alicyclic hydrocarbon is cyclohexane, the nitroalkane solvent is nitromethane, the arene solvent is selected from the group consisting of xylene and cumene, the alcohol solvent is selected from the group consisting of methanol, ethanol and isopropanol, the nitrile solvent is acetonitrile, the halohydrocarbon solvent is dichloromethane, the ketone solvent is acetone, the sulfoxide is dimethyl sulfoxide, the mixed solvent of one or more alcohol is selected from the group consisting of a mixed solvent of methanol and ethanol, a mixed solvent of methanol and isopropanol, and a mixed solvent of ethanol and isopropanol.

The present invention also provides a method for preparing the single crystal of crystal form D, characterized in that the method comprises the following steps of:

dissolving the compound of formula (I) in a solvent to crystallize, filtering and drying the resulting crystal to obtain the desired single crystal of crystal form D, wherein the solvent is a mixed solvent of an alcohol and water, the alcohol solvent is selected from the group consisting of methanol and ethanol; the ratio of the alcohol to water is 20:1-1:20, and preferably 6:1, and the crystallization method is selected from the group consisting of room temperature crystallization, cooling crystallization, solvent volatilization crystallization and crystallization induced by addition of a seed crystal.

The present invention also relates to a pharmaceutical composition of the crystal form A, B, C or D, characterized by further comprising one or more pharmaceutically acceptable carriers, diluents or excipients.

The present invention also relates to a use of the crystal form A, B, C or D, or the pharmaceutical composition in the preparation of a medicament for treating a disease associated with EZH2 inhibitor. According to the use of the present invention, the disease associated with EZH2 inhibitor is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma; preferably lymphoma, leukemia, breast cancer, lung cancer, prostate cancer, ovarian cancer, liver cancer, melanoma, rhabdoid tumor, synovial sarcoma and mesothelioma; the leukemia is preferably chronic myeloid leukemia, acute myeloid leukemia or mixed lineage leukemia; and the lymphoma is preferably non-Hodgkin lymphoma, diffuse large B-cell lymphoma or follicular lymphoma.

The resulting crystal forms of the compound of formula (I) are determined by X-ray powder diffraction spectrum (XRPD) and differential scanning calorimetry (DSC).

The recrystallization method for the crystal form is not particularly limited, and can be carried out by a conventional recrystallization process. For example, the material, i.e., the compound of formula (I), can be dissolved in an organic solvent followed by adding an anti-solvent to crystallize. After the completion of crystallization, the desired crystal can be obtained via filtering and drying.

The crystallization method of the present invention includes room temperature crystallization, cooling crystallization, solvent volatilization crystallization, crystallization induced by addition of a seed crystal and the like; and the cooling temperature is below 40° C., preferably from −10° C. to 40° C.

The starting material used in the method for preparing the crystal form of the present invention can be the compound of formula (I) in any form, and the specific forms include, but are not limited to, amorphous form, arbitrary crystal forms and the like.

Definitions

In the specification and claims of the present application, unless otherwise indicated, the scientific and technical terms used herein have the meanings generally understood by a person skilled in the art. However, in order to understand the present invention better, definitions and explanations of some related terms are provided. In addition, when the definitions and explanations of the terms provided in the present application are inconsistent with the meanings generally understood by a person skilled in the art, the definitions and explanations of the terms provided in the present application shall prevail.

The term "$C_{1-6}$alkyl" used in the present invention refers to a linear or branched alkyl containing 1 to 6 carbon atoms. Its specific examples include, but are not limited to: methyl, ethyl, n-propyl, isopropyl, n-butyl, isobutyl, sec-butyl, tent-butyl, n-pentyl, isopentyl, 2-methylbutyl, neo-pentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

The term "ether solvent" used in the present invention refers to a chain compound or a cyclic compound having an ether bond —O— and having 1 to 10 carbon atoms. Its specific examples include, but are not limited to: tetrahydrofuran, diethyl ether, propylene glycol methyl ether, methyl tent-butyl ether and 1,4-dioxane.

The term "alcohol solvent" used in the present invention refers to a group derived from the substitution of one or more hydrogen atoms on the "$C_{1-6}$ alkyl" by one or more "hydroxy", wherein the "hydroxy" and "$C_{1-6}$ alkyl" are as defined above. Its specific examples include, but are not limited to: methanol, ethanol, isopropanol, n-propanol, isopentanol and trifluoroethanol.

The term "ester solvent" used in the present invention refers to a combination of a lower organic acid having 1 to 4 carbon atoms and a lower alcohol having 1 to 6 carbon atoms. Its specific examples include, but are not limited to: ethyl acetate, isopropyl acetate or butyl acetate.

The term "ketone solvent" used in the present invention refers to a compound in which a carbonyl group (—C(O)—) is bonded to two hydrocarbon groups. Ketones can be classified into aliphatic ketones, alicyclic ketones, aromatic ketones, saturated ketones, and unsaturated ketones, depending on the hydrocarbon group in the molecule. Its specific examples include, but are not limited to: acetone, acetophenone, methyl isobutyl ketone or methyl pyrrolidone.

The term "nitrile solvent" used in the present invention refers to a group derived from the substitution of one or more hydrogen atoms on the "$C_{1-6}$ alkyl" by one or more "cyano", wherein the "cyano" and "$C_{1-6}$ alkyl" are as defined above. Its specific examples include, but are not limited to: acetonitrile or propionitrile.

The term "aliphatic hydrocarbon solvent" used in the present invention refers to a hydrocarbon compound having the basic properties of an aliphatic compound and having 1 to 10 carbon atoms, wherein the carbon atoms in the molecule are linked to a chain-like carbon skeleton in which the two ends are opened and do not form a ring, for example saturated aliphatic hydrocarbon, including alkane solvent. Its specific examples include, but are not limited to: n-butane, n-pentane, n-hexane or n-heptane.

The term " alicyclic hydrocarbon solvent" used in the present invention refers to a hydrocarbon compound having similar properties to aliphatic hydrocarbon and having a cyclic carbon skeleton with 1 to 8 ring atoms. Its specific examples include, but are not limited to: cyclopentane and cyclohexane.

The term "amide solvent" used in the present invention refers to a compound having a carbonyl amino (—C(O)N—) and having 1 to 10 carbon atoms. Its specific examples include, but are not limited to: N,N-dimethylformamide and N,N-dimethylacetamide.

The term "arene solvent" used in the present invention refers to a general term for a carbon ring compound and a derivative thereof, wherein the molecule has a conjugated system of a closed ring, and the number of π electrons conforms to the Huckel rule. Its specific examples include, but are not limited to: isopropylbenzene and xylene.

The term "halohydrocarbon solvent" used in the present invention refers to a group derived from "$C_{1-6}$alkyl" on which one or more hydrogen atoms are substituted by one or more "halogen atom", wherein the "halogen atom" and "$C_{1-6}$ alkyl" are as defined above. Its specific examples include, but are not limited to: methyl chloride, dichloromethane, chloroform and carbon tetrachloride.

The term "nitroalkane solvent" used in the present invention refers to a group derived from "$C_{1-6}$alkyl" on which one or more hydrogen atoms are substituted by one or more "nitro", wherein the "$C_{1-6}$alkyl" are as defined above. Its specific examples include, but are not limited to: nitromethane.

The term "mixed solvent" used in the present invention refers to a solvent obtained by mixing one or more different kinds of organic solvents in a certain ratio, or a solvent obtained by mixing an organic solvent and water in a certain ratio. The mixed solvent is preferably a mixed solvent of one or more alcohols, a mixed solvent of an alcohol and an ether, a mixed solvent of an alcohol and an aliphatic hydrocarbon, a mixed solvent of an ether and an aliphatic hydrocarbon, a mixed solvent of an alcohol and water, a mixed solvent of a halohydrocarbon and a nitrile, a mixed solvent of an amide and water, or a mixed solvent of an ether and water, wherein the alcohol, ether, aliphatic hydrocarbon, halohydrocarbon, amide and nitrile are as defined above.

The term "X-ray powder diffraction spectrum" or "XRPD" used in the present invention refers to a powder X-ray diffraction spectrum that is obtained according to the Bragg formula 2d sin θ=nλ (where λ is the wavelength of the X-ray, λ=1.54056Å, the order of diffraction n is any positive integer, generally taking the first-order diffraction peak, n=1), when the X-ray is incident on a certain atomic plane of a crystal or a partial crystal sample having a d-lattice plane spacing at a glancing angle θ (the complementary angle of incidence angle, also called the Bragg angle), the Bragg equation can be satisfied.

The term "differential scanning calorimetry" or "DSC" used in the present invention means to measure the temperature difference and heat flow difference between the sample and the reference during the heating or constant temperature process of the sample, to characterize all physical and chemical changes associated with the thermal effect, and to obtain phase change information of the sample.

The term "2θ" or "2θ angle" used in the present invention refers to the diffraction angle, θ is the Bragg angle, and the unit of which is ° or degree. The error range of 2θ is from ±0.1 to ±0.5, preferably from ±0.1 to ±0.3, and more preferably ±0.2.

The term "interplanar spacing" or "interplanar distance (d value)" used in the present invention means that the space lattice selects three unparallel unit vectors a, b, c, wherein each of them connects two adjacent lattice dots, and the three vectors divide the lattice into juxtaposed parallel juxtagonal units, called the interplanar spacing. The space lattice is divided according to the determined parallelepiped unit lines to obtain a set of linear grids, which is called a space lattice or a lattice. The lattice reflects the periodicity of the crystal structure with geometric points and lines. Different crystal planes have different interplanar spacings (i.e., distance between two adjacent parallel crystal planes); the unit is Å or angstrom.

The present invention also relates to a pharmaceutical composition comprising the crystal form A, B, C or D of the compound of formula (I) and optionally one or more pharmaceutically acceptable carriers and/or diluents. The pharmaceutical composition can be formulated into any one of pharmaceutically acceptable dosage forms. For example, the crystal form A, B, C or D of the compound of formula (I) or the pharmaceutical formulation of the present invention can be formulated into a tablet, capsule, pill, granule, solution, suspension, syrup, injection (including injection solution, sterile powder for injection, and concentrated solution for injection), suppository, inhalant or spray.

In addition, the pharmaceutical composition of the present invention can also be administrated to a patient or subject in need of such treatment by any suitable administration mode, such as oral, parenteral, rectal, intrapulmonary or topical administration. For oral administration, the pharmaceutical composition can be formulated into an oral formulation, for example, an oral solid formulation such as a tablet, capsule, pill, granule and the like; or an oral liquid formulation such as an oral solution, oral suspension, syrup and the like. When formulated into an oral formulation, the pharmaceutical composition can further comprise a suitable filler, binder, disintegrator, lubricant and the like. For parenteral administration, the pharmaceutical composition can be formulated into an injection formulation including an injection solution, sterile powder for injection and concentrated solution for injection. When formulated into an injection formulation, the pharmaceutical composition can be produced by a conventional method in current pharmaceutical industry. When an injection formulation is formulated, an additional agent may not be added to the pharmaceutical formulation, or a suitable additional agent may be added depending on the nature of the medicament. For rectal administration, the pharmaceutical composition can be formulated into a suppository and the like. For intrapulmonary administration, the pharmaceutical composition can be formulated into an inhalant or spray and the like. In certain preferred embodiments, the crystal form A, B, C or D of the compound of formula (I) of the present invention is present in the pharmaceutical composition or medicament in a therapeutically and/or prophylactically effective amount. In certain preferred embodiments, the crystal form A, B, C or D of the compound of formula (I) of the present invention is present in the pharmaceutical composition or medicament in unit dose.

The crystal form A, B, C or D of the compound of formula (I) of the present invention can be used to prepare a medicament for treating a disease associated with EZH2 inhibitor. Therefore, the present application also relates to a use of the crystal form A, B, C or D of the compound of formula (I) of the present invention in the preparation of a medicament for treating a disease associated with EZH2 inhibitor. Moreover, the present application also relates to a method for inhibiting a disease associated with EZH2 inhibitor, comprising administering a therapeutically and/or prophylactically effective amount of the crystal form A, B, C or D of the compound of formula (I) of the present invention or the pharmaceutical composition of the present invention to a subject in need thereof.

In certain preferred embodiments, the disease is a disease associated with EZH2 inhibitor selected from pain.

Advantageous Effects of the Present Invention

Compared with the prior art, the technical solution of the present invention has the following advantages:

Studies have shown that the crystal forms A, B, C and D of the compound of formula (I) prepared according to present invention have a good stability and high purity. The single crystals of crystal forms A and D are obtained. The crystal forms A, B, C and D of the compound of formula (I) prepared by the technical solution of the present invention can meet the production, transportation and storage requirements of drug products. Its preparation process is stable, repeatable and controllable, and can be adapted to industrial production.

DETAILED DESCRIPTION OF THE INVENTION

Figure 1:
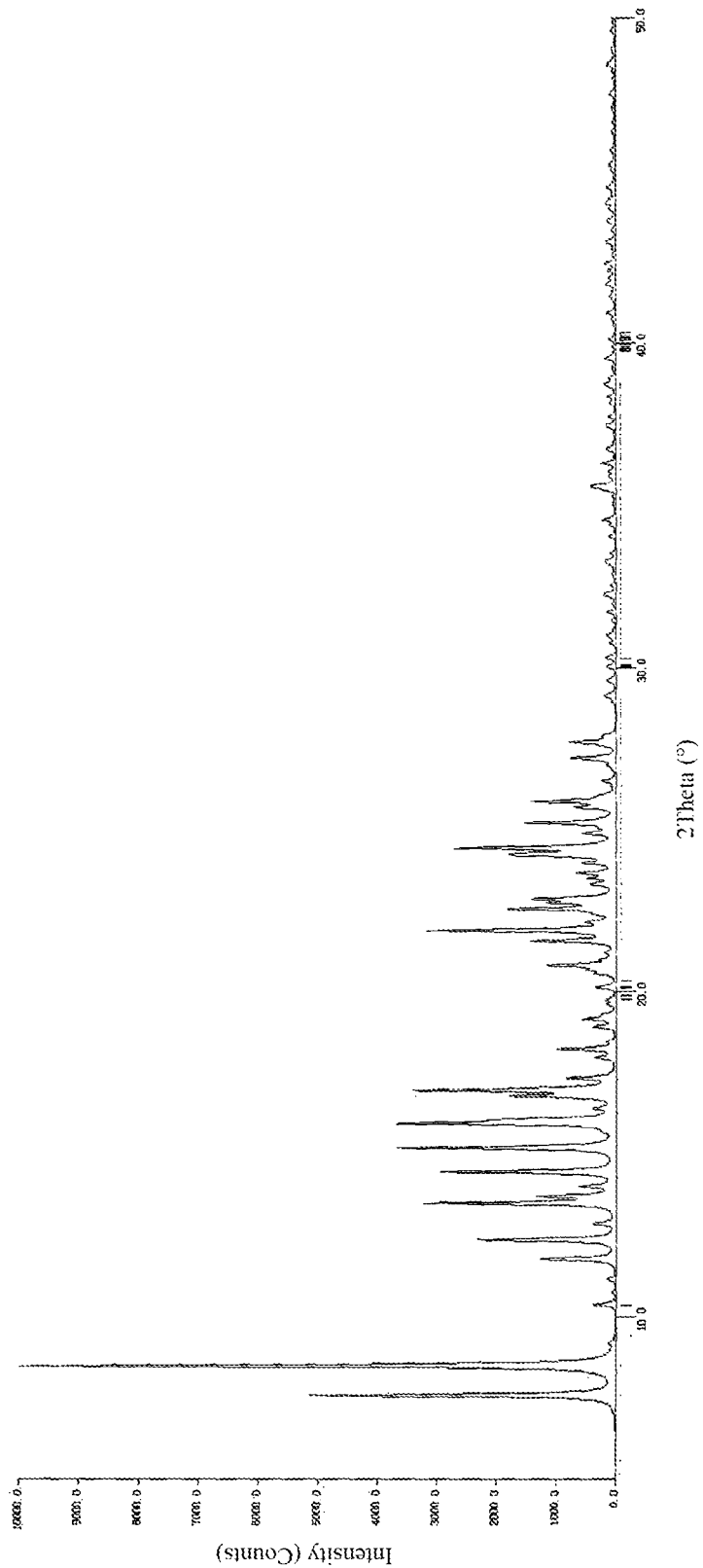
FIG. 1 shows the XRPD spectrum of crystal form A of the compound of formula (I).

The present invention will be illustrated by the following examples in detail. The examples of the present invention are merely intended to describe the technical solution of the present invention, and should not be considered as limiting the spirit and scope of the present invention.

Test conditions for the instruments used in the experiments:

1. Differential Scanning calorimeter, DSC

Instrument type: Mettler Toledo DSC3+ STAR$^e$ System

Purging gas: Nitrogen (50 mL/min)

Heating rate: 10.0° C./min

Temperature range: 20-250° C.

2. X-ray Powder Diffraction, XRPD

Instrument type: BRUKER D8 Discover A25 X-ray powder diffractometer

Ray: monochromatic Cu—Kα ray (λ=1.5406 Å)

Scanning mode: θ/2,θ Scanning range: 10-48°

Voltage: 40 kV, Electric current: 40 mA

3. Dynamic Vapour Sorption, DVS

Instrument type: DVS advantage

Temperature: 25° C.

Solvent: water

Humidity change: 0-95-0-95-0% RH, dm/dt=0.002

Comparative Example 1.

Preparation method in Example 2 of WO2017084494 (PCT/CN2016/104318)

Preparation of N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (the compound of formula (I))

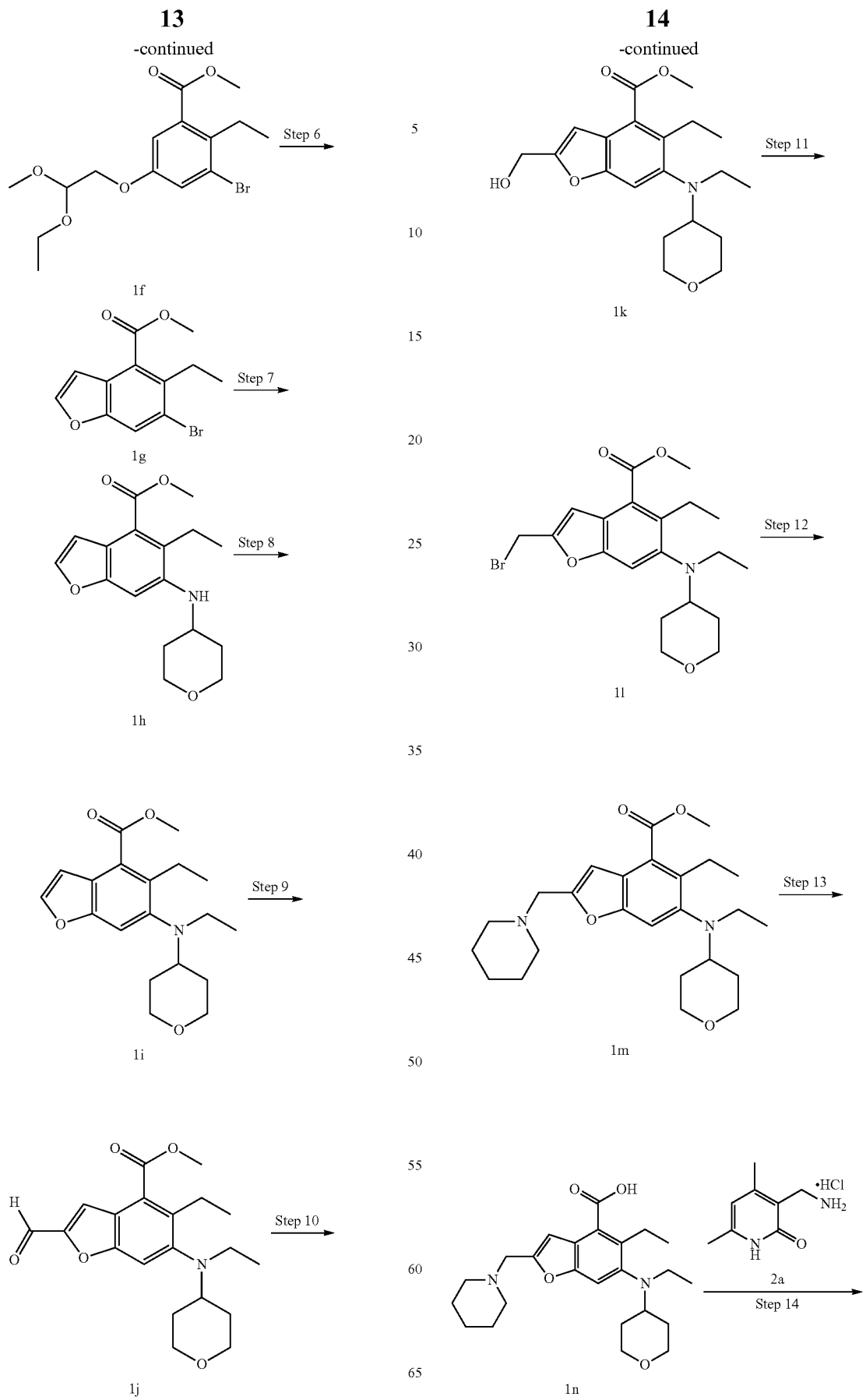

-continued

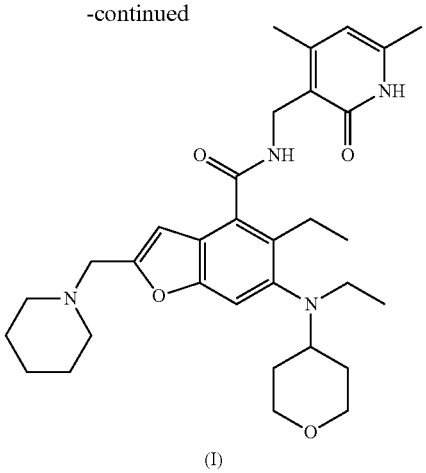

(I)

Step 1

3-Bromo-2-ethyl-5-nitrobenzoic acid 1b

2-Ethylbenzoic acid 1a (20.0 g, 133 mmol, prepared according to the method disclosed in "*Journal of the American Chemical Society,* 1991, 113(13), 4931-6") was added to 150 mL of sulfuric acid, and then sodium nitrate (11.3 g, 133 mmol) was added in batches in an ice bath. The reaction solution was stirred for 3 hours, and then N-bromosuccinimide (2.6 g, 14.5 mmol) was added in batches. The reaction mixture was stirred for 1 hour at 60° C. After the reaction was completed, the reaction solution was poured to ice water, stirred well and filtered. The filtrate was washed with water, and concentrated under reduced pressure to obtain the crude title product 3-bromo-2-ethyl-5-nitrobenzoic acid 1b (35 g) as a white solid, which was directly used in the next step without purification.

Step 2

Methyl 3-bromo-2-ethyl-5-nitrobenzoate 1c

The crude 3-bromo-2-ethyl-5-nitrobenzoic acid 1b (35 g, 128 mmol) was dissolved in 200 mL of N,N-dimethylformamide, then iodomethane (21.8 g, 153 mmol) and potassium carbonate (35.3 g, 255 mmol) were added. The reaction mixture was stirred for 2 hours at room temperature. After the reaction was completed, the reaction solution was concentrated under reduced pressure. The reaction solution was added with excess water, and extracted with ethyl acetate. The organic phases were combined, washed with water and saturated sodium chloride solution, dried over anhydrous sodium sulfate, and filtered. The filtrate was concentrated under reduced pressure to obtain the crude title product methyl 3-bromo-2-ethyl-5-nitrobenzoate 1c (36 g) as a yellow oil, which was directly used in the next step without purification.

Step 3

Methyl 5-amino-3-bromo-2-ethylbenzoate 1d

The crude methyl 3-bromo-2-ethyl-5-nitrobenzoate 1c (35.0 g, 121 mmol) was added to 250 mL of ethanol and 150 mL of water. The reaction solution was heated to 70° C., added with ammonium chloride (52.8 g, 969 mmol), then added with iron powder (34 g, 606 mmol) in batches. The reaction system was stirred for 2 hours at 70° C. After the reaction was completed, the reaction solution was filtered through celite while hot. The filter cake was washed with hot ethanol, then the filtrate was combined and concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-amino-3-bromo-2-ethylbenzoate 1d (22.0 g, yield 70%) as a yellow solid.

Step 4

Methyl 3-bromo-2-ethyl-5-hydroxybenzoate 1e

Methyl 5-amino-3-bromo-2-ethylbenzoate 1d (15.0 g, 58 mmol) was dissolved in 10 mL of acetonitrile, then 200 mL of 10% sulfuric acid was added. The reaction solution was stirred well and cooled to 3° C. in an ice-salt bath, then added dropwise with 10 mL of a pre-prepared solution of sodium nitrite (4.4 g, 64 mmol). The reaction solution was stirred for 4 hours at the above temperature, added dropwise with 200 mL of 50% sulfuric acid, then stirred for 1 hour at 90° C. After the reaction was completed, the reaction solution was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 3-bromo-2-ethyl-5-hydroxybenzoate 1e (5.5 g, yield 37%) as a brown solid.

Step 5

Methyl 3-bromo-5-(2,2-diethoxyethoxy)-2-ethylbenzoate 1f

Methyl 3-bromo-2-ethyl-5-hydroxybenzoate 1e (35 g, 135 mmol) was dissolved in 200 mL of N,N-dimethylformamide, then 2-bromo-1,1-diethoxyethane (40 g, 202 mmol) and potassium carbonate (37 g, 269 mmol) were added. The reaction system was stirred at 120° C. for 12 hours. After the reaction was completed, the reaction solution was concentrated under reduced pressure to remove N,N-dimethylformamide. The reaction solution was added with water, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 3-bromo-5-(2,2-diethoxyethoxy)-2-ethylbenzoate 1f (40 g, yield 80%) as a light yellow oil.

Step 6

Methyl 6-bromo-5-ethylbenzofuran-4-carboxylate 1g

Polyphosphoric acid (30 g) was added to 400 mL of toluene. The reaction solution was heated to 100° C., and added with 50 mL of a pre-prepared solution of methyl 3-bromo-5-(2,2-diethoxyethoxy)-2-ethylbenzoate 1f (40 g, 107 mmol) in toluene under stirring. The reaction solution was stirred for 16 hours at 100° C. After the reaction was completed, the supernatant was decanted. The residue was added with water and ethyl acetate. Two phases were separated, and the aqueous phase was extracted with ethyl acetate. The organic phases were combined, washed with saturated sodium carbonate solution and saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 6-bromo-5-ethylbenzofuran-4-carboxylate 1g (11.8 g, yield 39%) as a yellow solid.

Step 7

Methyl 5-ethyl-6-((tetrahydro-2H-pyran-4-y0amino) benzofuran-4-carboxylate 1h

Methyl 6-bromo-5-ethylbenzofuran-4-carboxylate ig (11.0 g, 39 mmol), tetrahydro-2H-pyran-4-amine (5.89 g, 58 mmol), tris(dibenzylideneacetone)dipalladium (3.6 g, 3.9 mmol), (0.9 mmol) bis(diphenylphosphino)-1,1'-binaphthalene (4.86 g, 7.8 mmol) and cesium carbonate (38 g, 117 mmol) were dissolved in 100 mL of toluene. The reaction solution was stirred for 12 hours at 100° C. After the reaction was completed, the reaction solution was filtered through celite, and the filter cake was washed with ethyl acetate. The organic phases were combined, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-((tetrahydro-2H-pyran-4-yl)amino)benzofuran-4-carboxylate 1h (10.0 g, yield 85%) as a yellow solid.

Step 8

Methyl 5-ethyl-6-(ethyl(tetrahydro-2H-pyran-4-y0amino)benzofuran-4-carboxylate 1i Methyl 5-ethyl-6-((tetrahydro-2H-pyran-4-yl)amino)benzofuran-4-carboxylate 1h (10.0 g, 0.033 mmol) was dissolved in 150 mL of 1,2-dichloroethane, then acetaldehyde (7.2 g, 0.165 mmol) and acetic acid (9.9 g, 0.165 mmol) were added. The reaction solution was stirred for 1 hour, and added with sodium triacetoxyborohydride (20.8 g, 0.1 mmol). The reaction solution was stirred for 12 hours at room temperature. After the reaction was completed, the reaction solution was concentrated under reduced pressure, neutralized with saturated sodium bicarbonate solution, and extracted with ethyl acetate.

The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl(tetrahydro-2H-pyran-4-yl)amino)benzofuran-4-carboxylate 1i (7.8 g, yield 71%) as a white solid.

MS m/z (LC-MS): 332.4 [M+1]

Step 9

Methyl 5-ethyl-6-(ethyl(tetrahydro-2H-pyran-4-yl) amino)-2-formylbenzofuran-4-carboxylate 1j Methyl 5-ethyl-6-(ethyl(tetrahydro-2H-pyran-4-yl) amino)benzofuran-4-carboxylate 1i (1.6 g, 4.8 mmol) was dissolved in 25 mL of tetrahydrofuran. The reaction solution was cooled to −70° C., and added dropwise with 2.0 M lithium diisopropylamide (3.6 mL, 7.3 mmol) under an argon atmosphere. The reaction solution was stirred for 90 minutes, and added with N,N-dimethylformamide (536 mg, 7.3 mmol). The reaction solution was stirred for 2 hours, then slowly warmed up to room temperature. The reaction solution was added with excess ammonium chloride, stirred well and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl(tetrahydro-2H-pyran-4-yl)amino)-2-formylbenzofuran-4-carboxylate 1j (1.3 g, yield 75%) as a yellow oil.

MS m/z (ESI):360.2 [M+1]

Step 10

Methyl 5-ethyl-6-(ethyl(tetrahydro-2H-pyran-4-yl) amino)-2-(hydroxymethyl)benzofuran-4-carboxylate 1k Methyl 5-ethyl-6-(ethyl(tetrahydro-2H-pyran-4-yl) amino)-2-formylbenzofuran-4-carboxylate 1j (1.4 g, 3.9 mmol) was dissolved in 5 mL of tetrahydrofuran and 10 mL of methanol, then sodium borohydride (222 mg, 5.8 mmol) was added. The reaction solution was stirred for 30 minutes at room temperature. After the reaction was completed, the reaction solution was concentrated under reduced pressure, added with water and saturated sodium bicarbonate solution, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl (tetrahydro-2H-pyran-4-yl)amino)-2-(hydroxymethyl)benzofuran-4-carboxylate 1k (1.4 g, yield 99%) as a yellow oil.

Step 11

Methyl 2-(bromomethyl)-5-ethyl-6-(ethyl(tetrahydro-2H-pyran-4-yl)amino)benzofuran-4-carboxylate 11

Methyl 5-ethyl-6-(ethyl(tetrahydro-2H-pyran-4-yl) amino)-2-(hydroxylmethyl) benzofuran-4-carboxylate 1k (1.0 g, 2.8 mmol) was dissolved in 30 mL of tetrahydrofuran, then phosphorus tribromide (1.12 g, 4.2 mmol) was added dropwise. The reaction solution was stirred for 12 hours at room temperature. After the reaction was completed, the reaction solution was neutralized with saturated sodium bicarbonate solution, and extracted with ethyl acetate three times. The organic phases were combined, washed with saturated sodium chloride solution, dried over anhydrous sodium sulfate, and filtered. The filtrate was concentrated under reduced pressure to obtain the crude title product methyl 2-(bromomethyl)-5-ethyl-6-(ethyl(tetrahydro-2H-pyran-4-yl)amino)benzofuran-4-carbo xylate 11 (1.15 g) as a yellow oil, which was directly used in the next step without purification.

Step 12

Methyl5-ethyl-6-(ethyl(tetrahydro-2H-pyran-4-yl) amino)-2-(piperidin-1-ylmethyl)benzofuran-4-carboxylate 1m The crude methyl 2-(bromomethyl)-5-ethyl-6-(ethyl(tetrahydro-2H-pyran-4-yl)amino)benzofuran-4-carbo xylate 11 (1.15 g, 2.7 mmol) was dissolved in 15 mL of acetonitrile, then 10 mL of a pre-prepared solution of piperidine (362 mg, 4.3 mmol) in acetonitrile were added dropwise. The reaction solution was stirred for 30 minutes at room temperature. After the reaction was completed, the reaction solution was concentrated under reduced pressure, and added with ethyl acetate and saturated sodium bicarbonate solution. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with dichloromethane and methanol as the eluent to obtain the title product methyl 5 -ethyl-6-(ethyl(tetrahydro-2H-pyran-4-yl)amino)-2-(piperidin-1-ylmethyl)benzofuran-4-carboxylate 1m (1.2 g, yield 99%) as a yellow oil.

MS m/z (LC-MS): 429.2[M+1]

Step 13

5-Ethyl-6-(ethyl(tetrahydro-2H-pyran-4-yl)amino)-2-(piperidin-1-ylmethyl)benzofuran-4-carboxylic acid 1n Methyl 5-ethyl-6-(ethyl(tetrahydro-2H-pyran-4-yl) amino)-2-(piperidin-1-ylmethyl) benzofuran-4-carboxylate 1m (1.2 g, 2.7 mmol) was dissolved in 5 mL of tetrahydrofuran and 20 mL of methanol, then 5 mL of 4 M sodium hydroxide solution were added. The reaction solution was stirred for 12 hours at 60° C. After the reaction was completed, concentrated hydrochloric acid was added to adjust the pH of the reaction solution to 4. The mixture was concentrated under reduced pressure, and the residue was dissolved in a mixed solvent of dichloromethane and methanol (V:V=5:1) and filtered. The filter cake was washed with a mixed solvent of dichloromethane and methanol (V:V=5:1). The filtrates were combined, and concentrated under reduced pressure to obtain the crude title product 5-ethyl-6-(ethyl(tetrahydro-2H-pyran-4-yl)amino)-2-(piperidin-1-ylmethyl)benzofuran-4-carboxylic acid 1n (1.1 g) as a yellow solid, which was directly used in the next step without purification.

MS m/z (LC-MS): 415.2[M+1]

Step 14

N-((4,6-dimethyl-2-oxo-1,2-dihydropyridin-3 -yl) methyl)5-ethyl-6-(ethyl(tetrahydro-2H-pyran-4-yl)amino)-2-(piperidin-1-ylmethyl)benzofuran-4-carboxamide (the compound of formula (I)) 5-Ethyl-6-(ethyl(tetrahydro-2H-pyran-4-yl)amino)-2-(piperidin-1-ylmethyl)benzof uran-4-carboxylic acid in (1.0 g, 2.4 mmol) was dissolved in 30 mL of N,N-dimethylformamide, then 1-ethyl-3-(3-dimethylaminopropyl)carbodiimide (696 mg, 3.6 mmol), 1-hydroxybenzotriazole (490 mg, 3.6 mmol) and N,N-diisopropylethylamine (1.56 g, 12.1 mmol) were added. The reaction solution was stirred for 1 hour, then added with 3-(aminomethyl)-4,6-dimethylpyridin-2(1H)-one hydrochloride 2a (593 mg, 3.0 mmol, prepared according to the method disclosed in the patent application "WO2014097041"). The reaction solution was stirred for 12 hours at room temperature. After the reaction was completed, the reaction solution was added with excess water, and extracted with a mixed solvent of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by silica gel column chromatography with dichloromethane and methanol as the eluent to obtain the title product N-((4,6-dimethyl-2-oxo-1,2-dihy dropyridin-3 -yl)methyl)-5-ethyl-6-(ethyl(tetrahy dro-2 H-pyran-4-yl)amino)-2-(piperidin-1-ylmethyl)benzofuran-4-carboxamide (I) (750 mg, yield 57%) as a white solid.

MS m/z (ESI): 549.7 [M+1]

Figure 17:
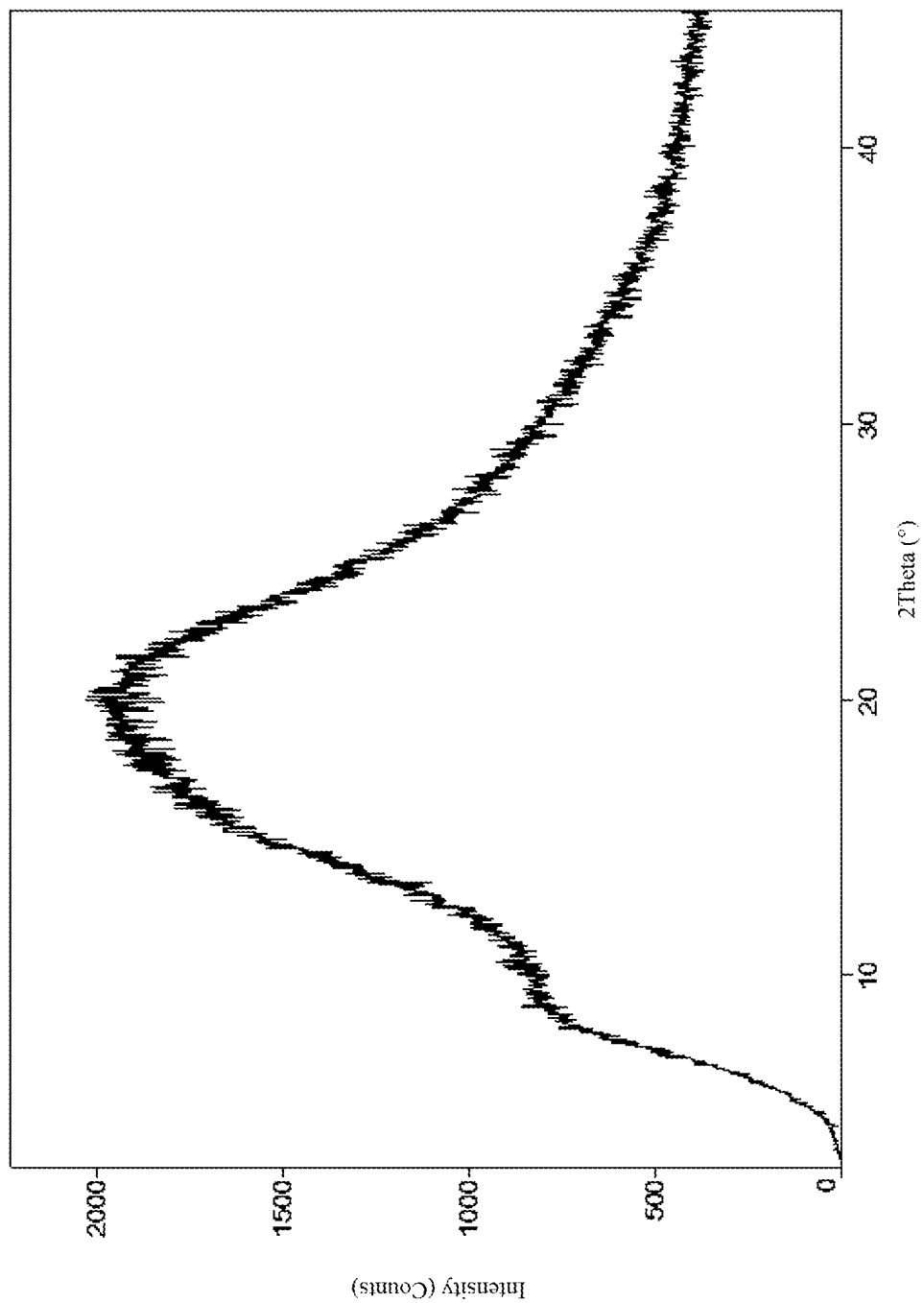
FIG. 17 shows the XRPD spectrum of amorphous form of the compound of formula (I).

The white solid product was identified as amorphous form by XRPD spectrum. The XRPD spectrum of the amorphous form is shown in FIG. 17.

EXAMPLE 1

Preparation of Crystal Form A

The crude produfct N-((4,6-dimethyl-2-oxo-1,2-dihy dropyridin-3 -yl)methyl)-5-ethyl-6-(ethyl(tetrahydro-2 H-pyran-4-yl)amino)-2-(piperidin-1-ylmethyl)benzofuran-4-carboxamide (20 mg, 0.036 mmol) obtained in Comparative example 1 was added to a reaction flask, and a mixed solvent of dichloromethane-acetonitrile (v:v, 1:10, 500 μL) was added. The reaction solution was stirred at 25° C. for one hour, and filtrated. The filtrate was placed in a clean flask, and slowly volatilized until the solvent was completely dried to obtain a white to pale yellow solid. The XRPD spectrum of the solid sample is shown in FIG. 1, and the characteristic peak positions are shown in the following table:

TABLE 1

| Characteristic peaks of crystal form A | | |
|---|---|---|
| Peak No. | 2θ[°] | d[Å] |
| Peak 1 | 7.60 | 11.62 |
| Peak 2 | 8.51 | 10.38 |
| Peak 3 | 10.37 | 8.53 |
| Peak 4 | 11.16 | 7.92 |
| Peak 5 | 11.80 | 7.5 |
| Peak 6 | 12.38 | 7.14 |
| Peak 7 | 12.89 | 6.86 |
| Peak 8 | 13.52 | 6.55 |
| Peak 9 | 13.73 | 6.44 |
| Peak 10 | 14.03 | 6.31 |
| Peak 11 | 14.48 | 6.11 |
| Peak 12 | 15.23 | 5.81 |
| Peak 13 | 15.99 | 5.54 |
| Peak 14 | 16.10 | 5.5 |
| Peak 15 | 16.43 | 5.39 |
| Peak 16 | 16.82 | 5.27 |
| Peak 17 | 16.99 | 5.21 |

TABLE 1-continued

Characteristic peaks of crystal form A

| Peak No. | 2θ[°] | d[Å] |
|---|---|---|
| Peak 18 | 17.35 | 5.11 |
| Peak 19 | 18.24 | 4.86 |
| Peak 20 | 18.92 | 4.69 |
| Peak 21 | 19.17 | 4.63 |
| Peak 22 | 20.68 | 4.29 |
| Peak 23 | 20.82 | 4.26 |
| Peak 24 | 21.57 | 4.12 |
| Peak 25 | 21.91 | 4.05 |
| Peak 26 | 22.57 | 3.94 |
| Peak 27 | 22.76 | 3.90 |
| Peak 28 | 22.88 | 3.88 |
| Peak 29 | 23.53 | 3.78 |
| Peak 30 | 23.68 | 3.75 |
| Peak 31 | 24.00 | 3.71 |
| Peak 32 | 24.29 | 3.66 |
| Peak 33 | 24.47 | 3.64 |
| Peak 34 | 24.91 | 3.57 |
| Peak 35 | 25.24 | 3.53 |
| Peak 36 | 25.72 | 3.46 |
| Peak 37 | 25.90 | 3.44 |
| Peak 38 | 27.23 | 3.27 |
| Peak 39 | 27.74 | 3.21 |
| Peak 40 | 35.63 | 2.52 |

EXAMPLE 2

Preparation of Single Crystal of Crystal Form A

Figure 15:
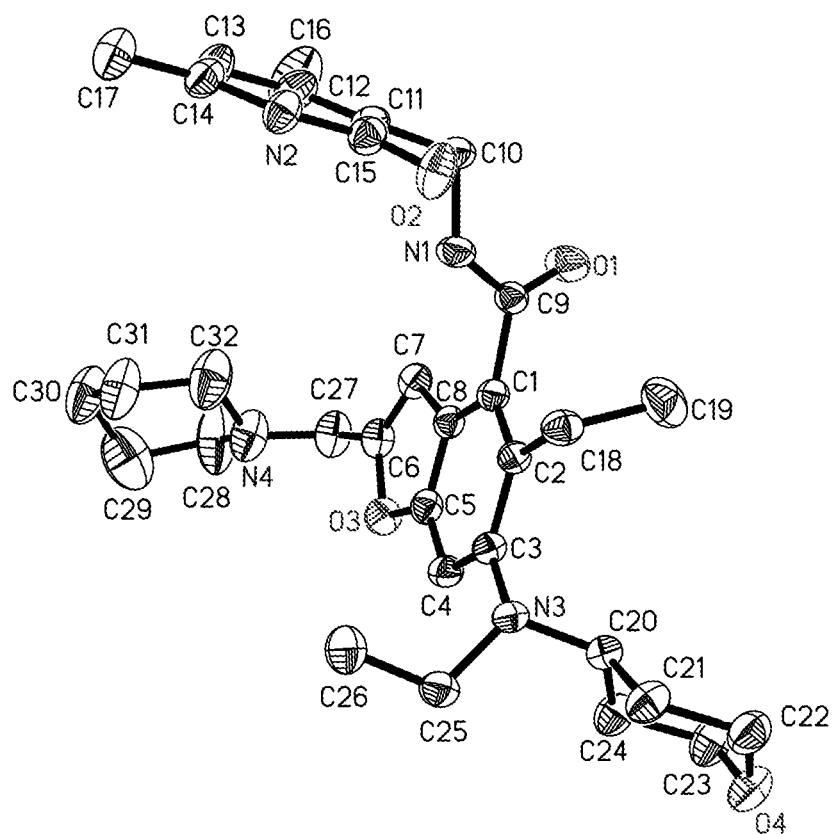
FIG. 15 shows the X-ray single crystal diffraction molecular stereostructure diagram of crystal form A of the compound of formula (I).

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dissolved in a mixed solvent of acetonitrile and dichloromethane (v/v, 10:1, 1 mL). The mouth of the flask was sealed by a sealing film which was punctured two to three small holes. The solvent was volatilized to obtain a single crystal. The single molecular stereostructure of the crystal sample is shown in FIG. 15 by single crystal X-ray diffraction (XRD), and the unit cell parameters are shown in the following table:

TABLE 2

Unit cell parameters of single crystal of crystal form A

| Parameters | | Values |
|---|---|---|
| Crystal system | | Orthorhombic crystal system |
| Space group | | P bca |
| Unit cell parameters | a (Å) | 17.051(3) |
| | b (Å) | 15.840(3) |
| | c (Å) | 23.2549(5) |
| | α (°) | 90.0 |
| | β (°) | 90.0 |
| | γ (°) | 90.0 |
| Unit cell volume V (Å$^3$) | | 6279(2) |
| Z (Asymmetric unit number in unit cell) | | 8 |
| Calculated density (g/cm$^3$) | | 1.161 |

EXAMPLE 3

Preparation of Crystal Form B

Figure 2:
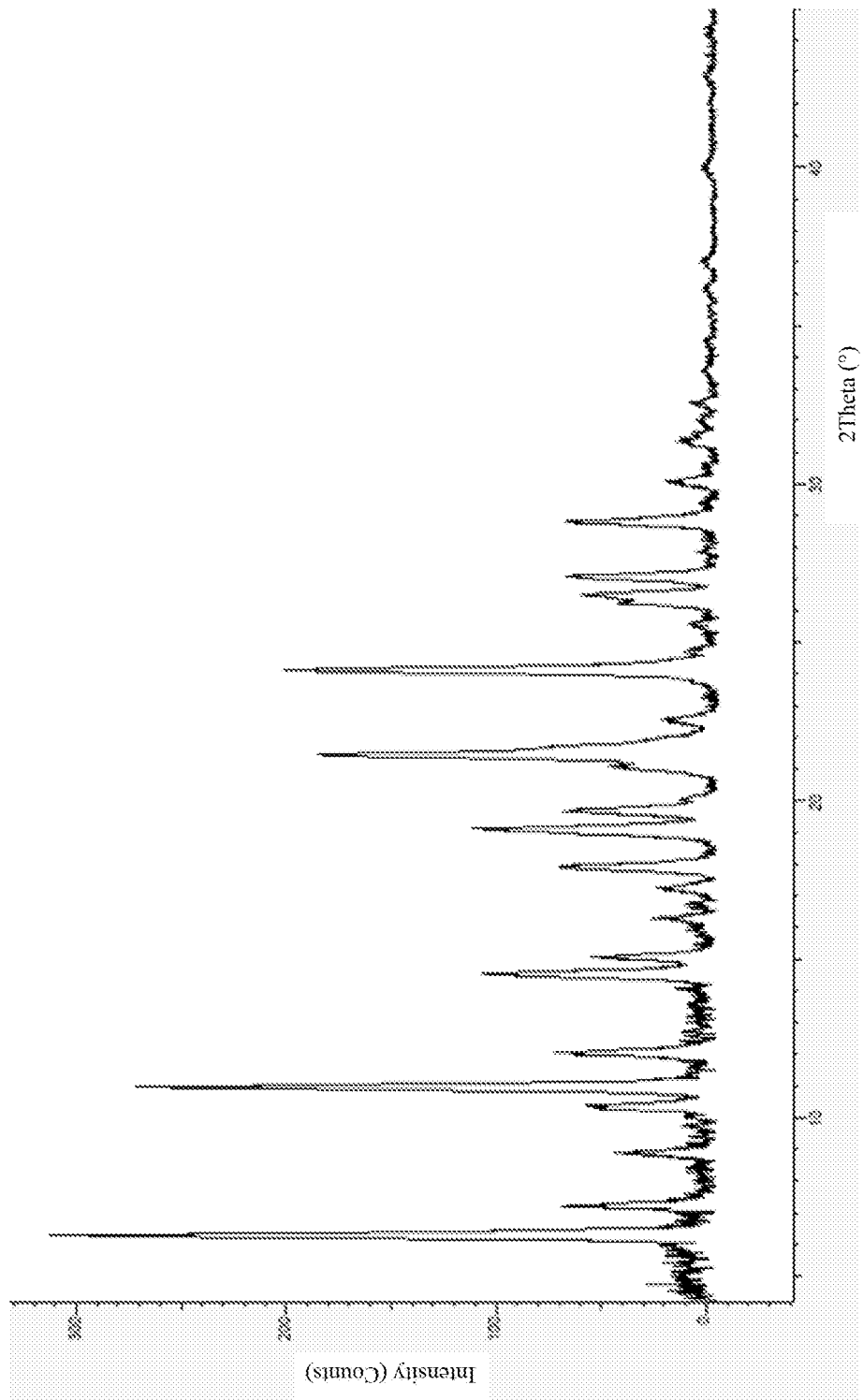
FIG. 2 shows the XRPD spectrum of crystal form B of the compound of formula (I).
Figure 3:
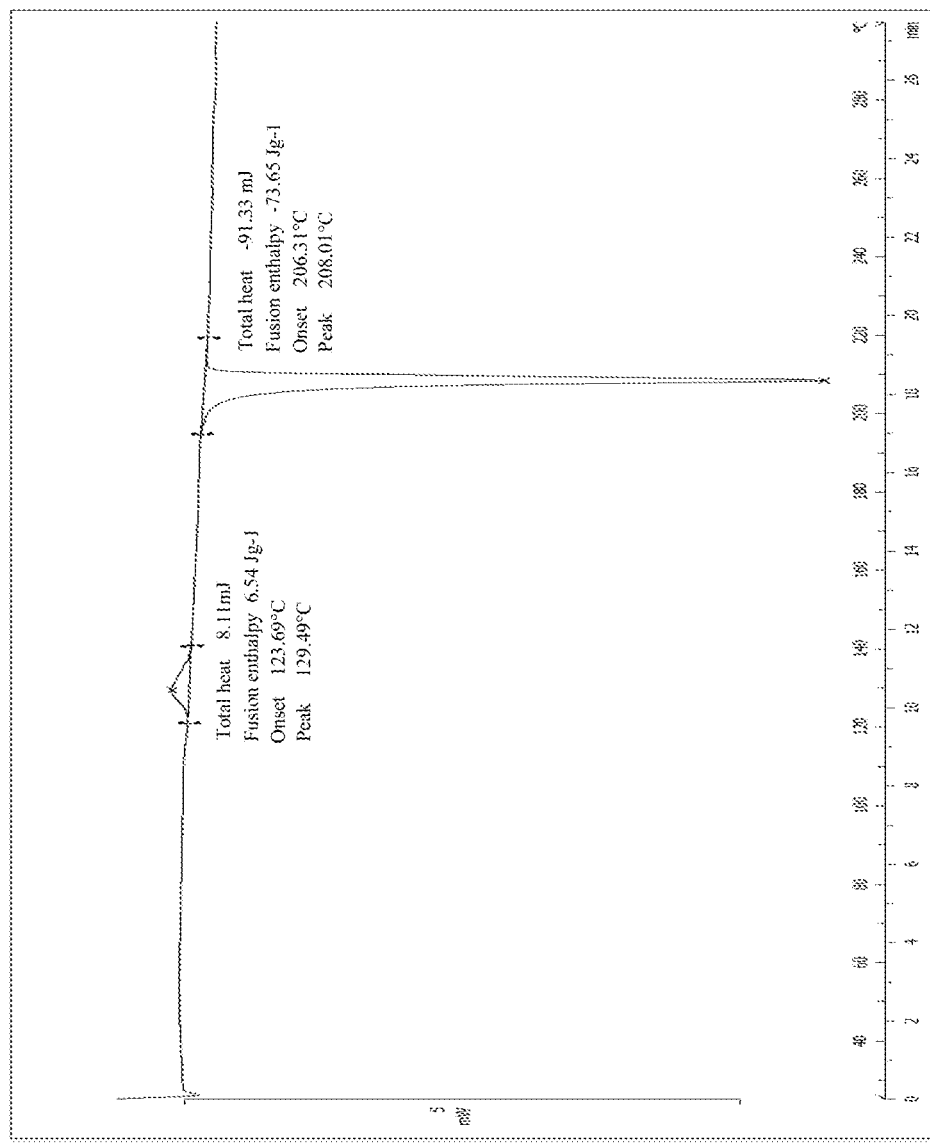
FIG. 3 shows the DSC spectrum of crystal form B of the compound of formula (I).

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dissolved in ethanol (300 μL). The mouth of the flask was sealed by a sealing film which was punctured two to three small holes. The solution was placed still at room temperature until the solvent volatilized to dryness to obtain a white to pale yellow solid. The XRPD spectrum of the crystal sample is shown in FIG. 2. The DSC spectrum is shown in FIG. 3, in which there are one endothermic peak and one exothermic during the temperature-rise period, the onset of the exothermic peak is at about 123.69° C., and the onset melting temperature is about 206.31° C. The crystal form was defined as crystal form B, and the characteristic peak positions are shown in the following table:

TABLE 3

Characteristic peaks of crystal form B

| Peak No. | 2θ[°] | d[Å] |
|---|---|---|
| Peak 1 | 6.31 | 13.99 |
| Peak 2 | 7.24 | 12.19 |
| Peak 3 | 8.92 | 9.90 |
| Peak 4 | 10.38 | 8.52 |
| Peak 5 | 10.99 | 8.04 |
| Peak 6 | 12.07 | 7.33 |
| Peak 7 | 14.56 | 6.08 |
| Peak 8 | 15.10 | 5.86 |
| Peak 9 | 16.36 | 5.42 |
| Peak 10 | 17.29 | 5.12 |
| Peak 11 | 17.94 | 4.94 |
| Peak 12 | 19.13 | 4.64 |
| Peak 13 | 19.71 | 4.50 |
| Peak 14 | 21.12 | 4.20 |
| Peak 15 | 21.48 | 4.13 |
| Peak 16 | 22.59 | 3.93 |
| Peak 17 | 24.15 | 3.68 |
| Peak 18 | 25.45 | 3.50 |
| Peak 19 | 26.28 | 3.39 |
| Peak 20 | 26.52 | 3.36 |
| Peak 21 | 27.10 | 3.29 |
| Peak 22 | 28.83 | 3.09 |
| Peak 23 | 30.07 | 2.97 |
| Peak 24 | 31.37 | 2.85 |
| Peak 25 | 32.56 | 2.75 |
| Peak 26 | 33.65 | 2.66 |
| Peak 27 | 34.64 | 2.59 |
| Peak 28 | 36.09 | 2.49 |
| Peak 29 | 37.13 | 2.42 |
| Peak 30 | 40.04 | 2.25 |

EXAMPLE 4

Preparation of Crystal Form B

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dissolved in ethanol (300 μL). The solution was added with water (900 μL) as an anti-solvent to precipitate a crystal. The mixture was filtered and dried to obtain a pale yellow solid. The crystal sample was identified as crystal form B by XRPD.

EXAMPLE 5

Preparation of Crystal Form C

Figure 4:
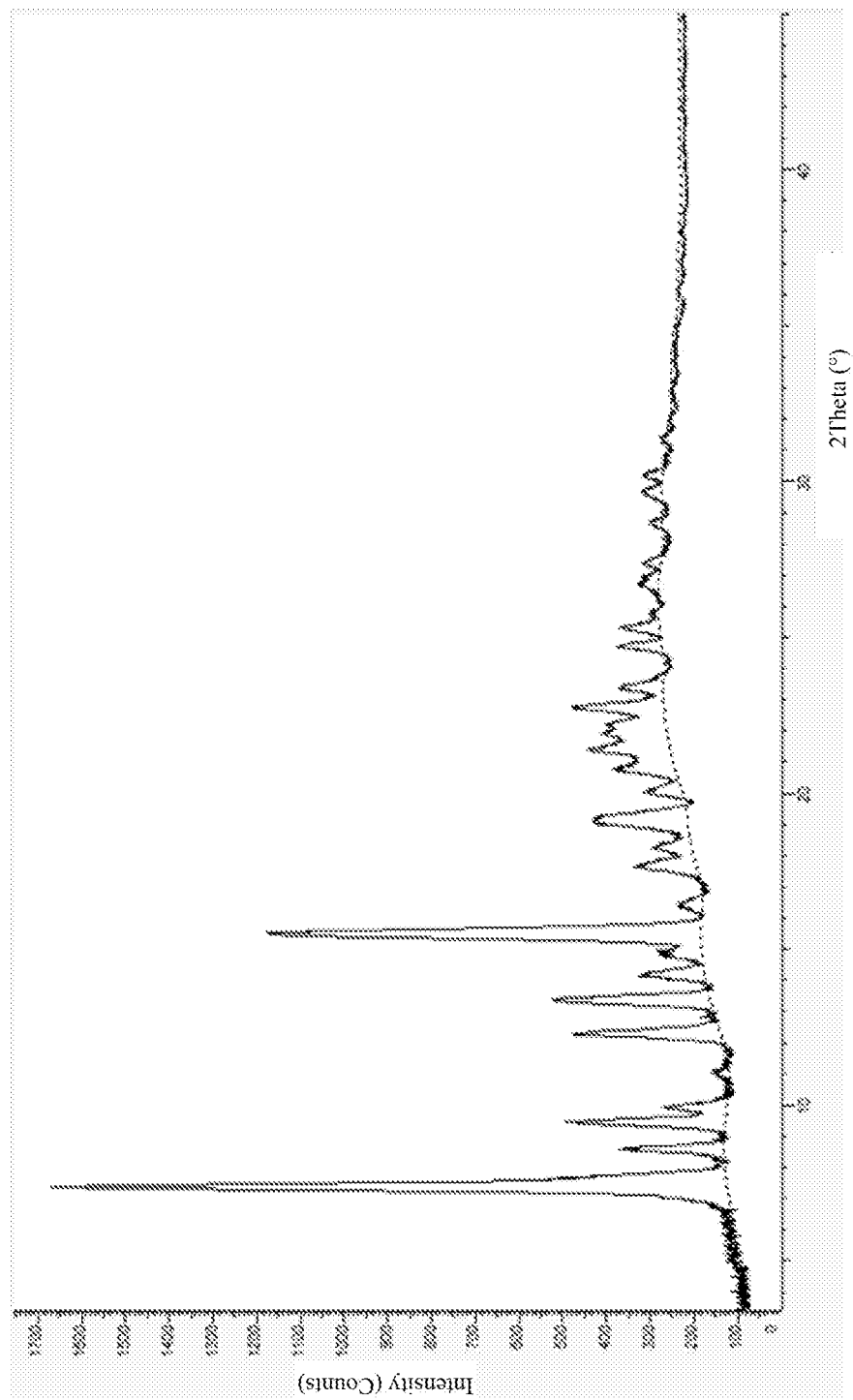
FIG. 4 shows the XRPD spectrum of crystal form C of the compound of formula (I).
Figure 5:
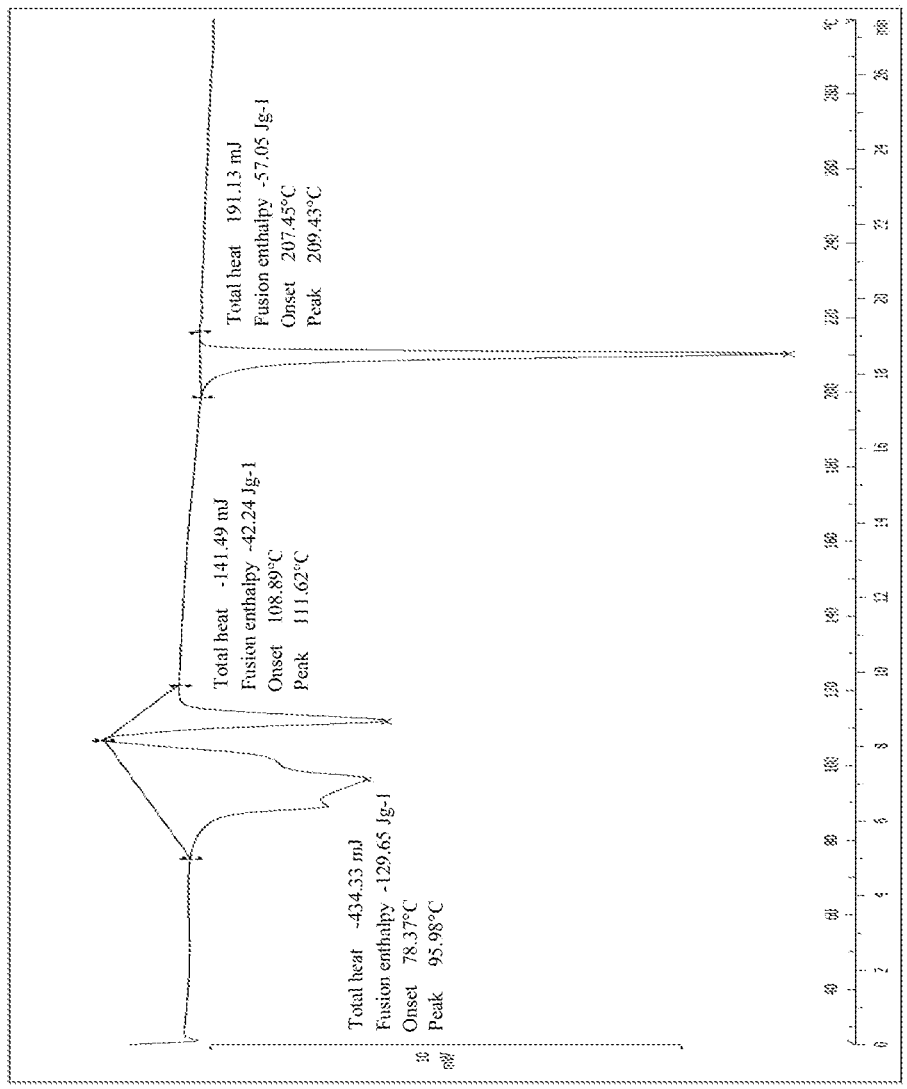
FIG. 5 shows the DSC spectrum of crystal form C of the compound of formula

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran- 4-carboxamide (30 mg, 0.055 mmol) obtained in Comparative example 1 was added to a reaction flask, and dissolved in 1,4-dioxane (1 mL). The solution was added with n-heptane (2 mL) to precipitate a crystal. The mixture was filtered and dried to obtain a white to pale yellow powder. The XRPD spectrum of the crystal sample is shown in FIG. 4. The DSC spectrum is shown in FIG. 5, in which there are multiple endothermic peaks. The crystal form was defined as crystal form C, and the characteristic peak positions are shown in the following table:

TABLE 4

Characteristic peaks of crystal form C

| Peak No. | 2θ[°] | d[Å] |
|---|---|---|
| Peak 1 | 7.40 | 11.93 |
| Peak 2 | 8.62 | 10.25 |
| Peak 3 | 9.49 | 9.32 |
| Peak 4 | 9.96 | 8.88 |
| Peak 5 | 11.12 | 7.95 |
| Peak 6 | 12.32 | 7.18 |
| Peak 7 | 13.39 | 6.61 |
| Peak 8 | 14.21 | 6.23 |
| Peak 9 | 14.85 | 5.96 |
| Peak 10 | 15.52 | 5.71 |
| Peak 11 | 16.50 | 5.37 |
| Peak 12 | 17.67 | 5.01 |
| Peak 13 | 18.28 | 4.85 |
| Peak 14 | 19.15 | 4.63 |
| Peak 15 | 19.17 | 4.63 |
| Peak 16 | 20.06 | 4.42 |
| Peak 17 | 20.80 | 4.27 |
| Peak 18 | 21.42 | 4.15 |
| Peak 19 | 21.89 | 4.06 |
| Peak 20 | 22.20 | 4.00 |
| Peak 21 | 22.78 | 3.90 |
| Peak 22 | 23.41 | 3.80 |
| Peak 23 | 24.74 | 3.60 |
| Peak 24 | 25.34 | 3.51 |
| Peak 25 | 26.70 | 3.34 |
| Peak 26 | 27.38 | 3.25 |
| Peak 27 | 28.64 | 3.11 |
| Peak 28 | 29.63 | 3.01 |
| Peak 29 | 30.20 | 2.96 |
| Peak 30 | 31.15 | 2.87 |

EXAMPLE 6

Preparation of Crystal Form D

Figure 6:
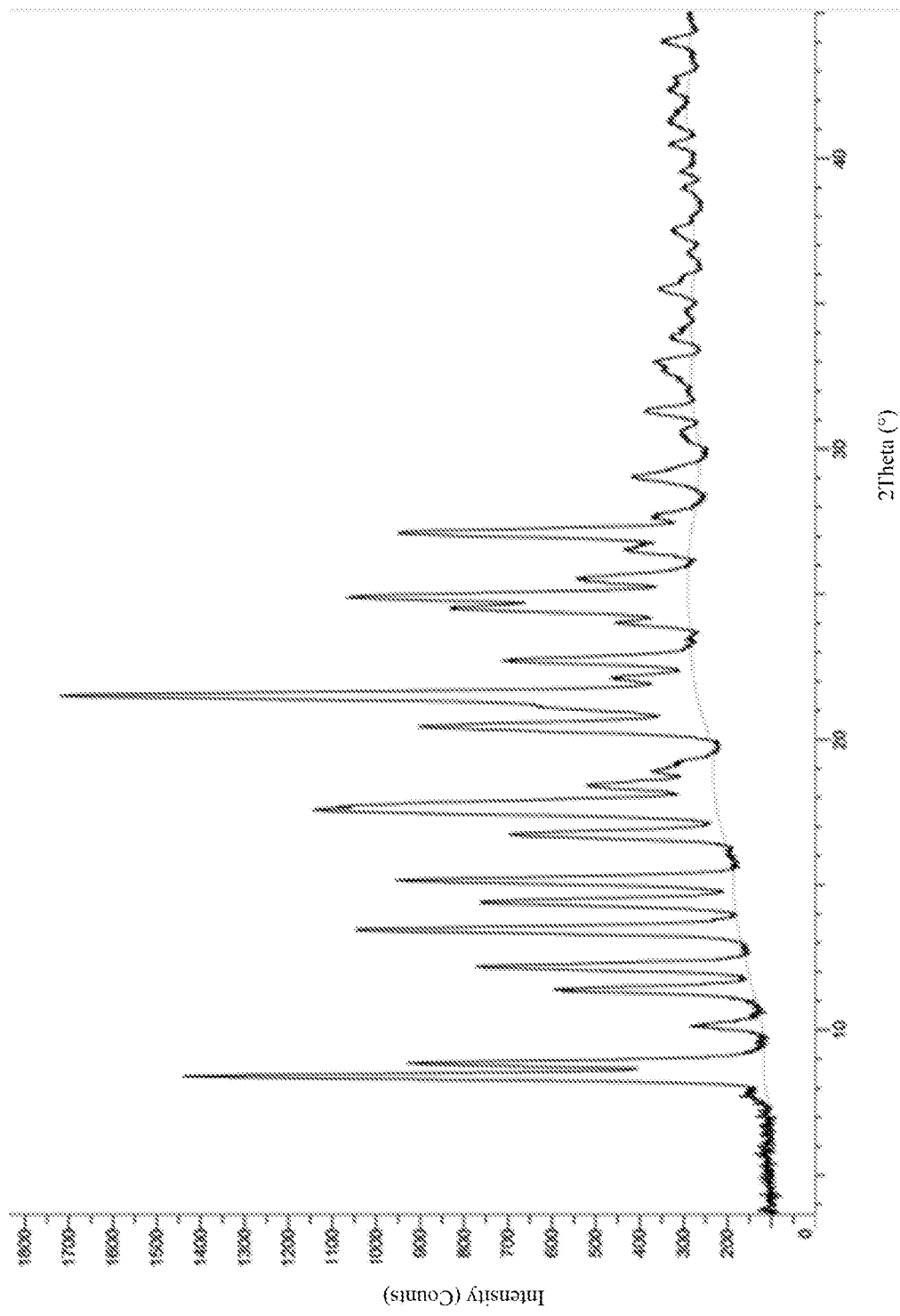
FIG. 6 shows the XRPD spectrum of crystal form D of the compound of formula
Figure 7:
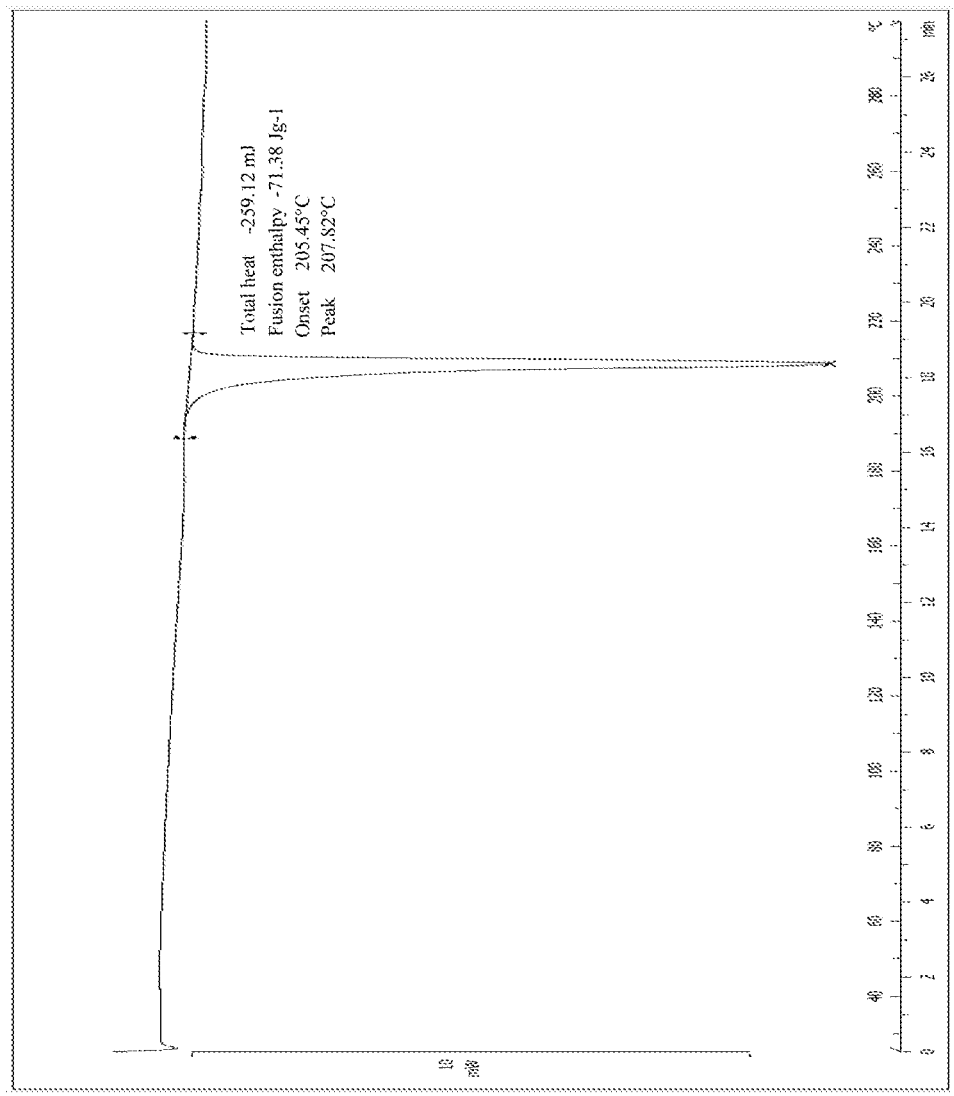
FIG. 7 shows the DSC spectrum of crystal form D of the compound of formula
Figure 8:
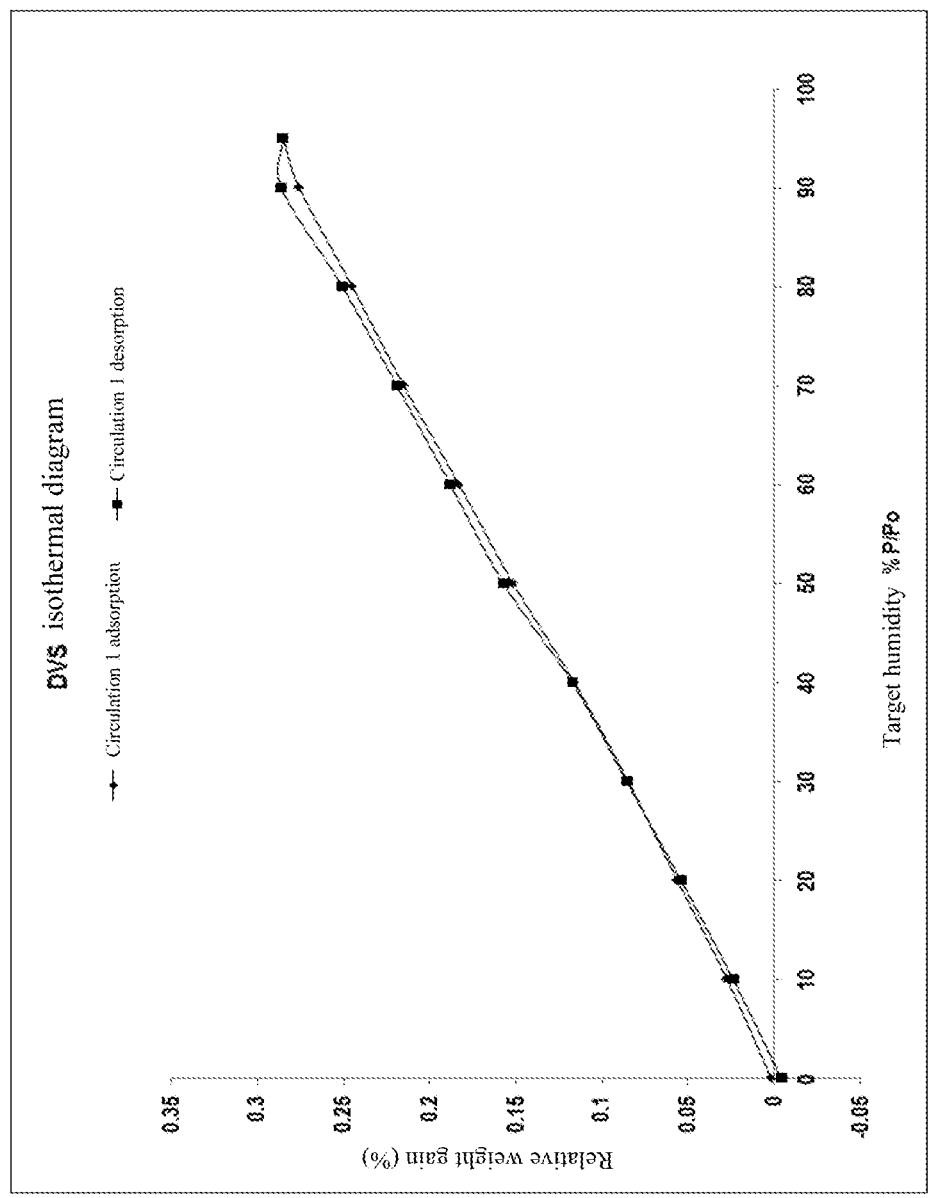
FIG. 8 shows the DVS circulation 1 diagram of crystal form D of the compound of formula (I).
Figure 9:
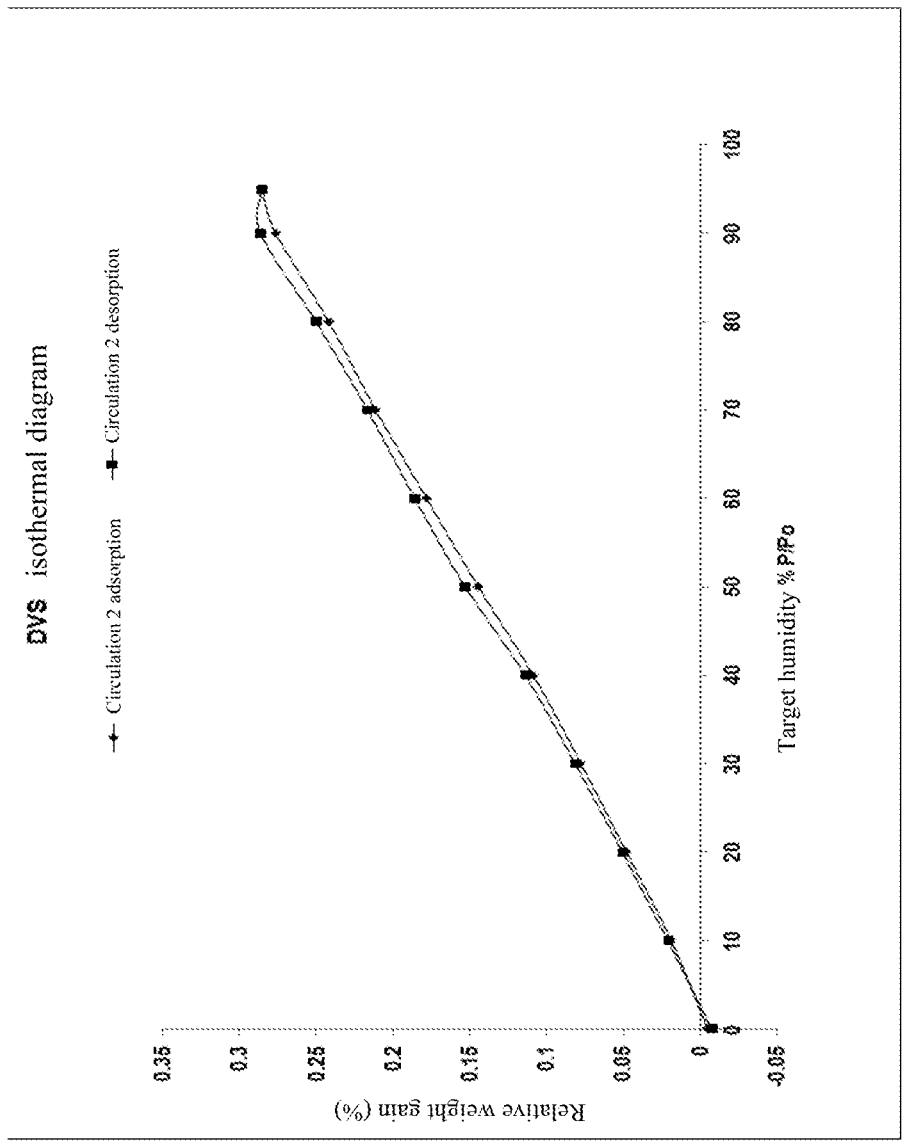
FIG. 9 shows the DVS circulation 2 diagram of crystal form D of the compound of formula (I).

The crude product N-((4,6-dimethyl-2-oxo-1,2-dihydropyridin-3 -yl)methyl)-5 -ethyl-6-(ethyl(tetrahydro-2 H-pyran-4-yl)amino)-2-(piperidin-1-ylmethyl)benzofuran-4-carboxamide (50 mg, 0.091 mmol) obtained in Comparative example 1 was added to a reaction flask, and methanol (100 μL) was added. The solution was stirred at 25° C. for five days, filtrated and dried under vacuum to obtain a white to pale yellow powder. The XRPD spectrum of the crystal sample is shown in FIG. 6. The DSC spectrum is shown in FIG. 7, in which the onset melting temperature is about 205.45° C. The crystal form was defined as crystal form D. It can be seen from the DVS diagrams of FIGS. 8 and 9 that the crystal form D has no obvious hygroscopicity. The characteristic peak positions are shown in the following table:

TABLE 5

Characteristic peaks of crystal form D

| Peak No. | 2θ[°] | d[Å] |
|---|---|---|
| Peak 1 | 8.41 | 10.50 |
| Peak 2 | 8.85 | 9.98 |
| Peak 3 | 10.15 | 8.71 |
| Peak 4 | 11.38 | 7.77 |
| Peak 5 | 12.18 | 7.26 |
| Peak 6 | 13.45 | 6.58 |
| Peak 7 | 14.40 | 6.14 |
| Peak 8 | 15.15 | 5.84 |
| Peak 9 | 16.73 | 5.29 |
| Peak 10 | 17.59 | 5.04 |
| Peak 11 | 17.68 | 5.01 |
| Peak 12 | 18.42 | 4.81 |
| Peak 13 | 18.91 | 4.69 |
| Peak 14 | 19.22 | 4.61 |
| Peak 15 | 20.45 | 4.34 |
| Peak 16 | 21.15 | 4.20 |
| Peak 17 | 21.51 | 4.13 |
| Peak 18 | 22.11 | 4.02 |
| Peak 19 | 22.72 | 3.91 |
| Peak 20 | 24.03 | 3.70 |
| Peak 21 | 24.53 | 3.63 |
| Peak 22 | 24.91 | 3.57 |
| Peak 23 | 25.54 | 3.49 |
| Peak 24 | 26.54 | 3.36 |
| Peak 25 | 27.11 | 3.29 |
| Peak 26 | 27.61 | 3.23 |
| Peak 27 | 29.04 | 3.07 |
| Peak 28 | 30.49 | 2.93 |
| Peak 29 | 31.31 | 2.85 |
| Peak 30 | 33.00 | 2.71 |
| Peak 31 | 33.88 | 2.64 |
| Peak 32 | 35.52 | 2.53 |
| Peak 33 | 37.53 | 2.39 |
| Peak 34 | 40.46 | 2.23 |
| Peak 35 | 41.36 | 2.18 |
| Peak 36 | 42.40 | 2.13 |
| Peak 37 | 44.02 | 2.06 |

Example 7

Preparation of Single Crystal of Crystal Form D

Figure 16:
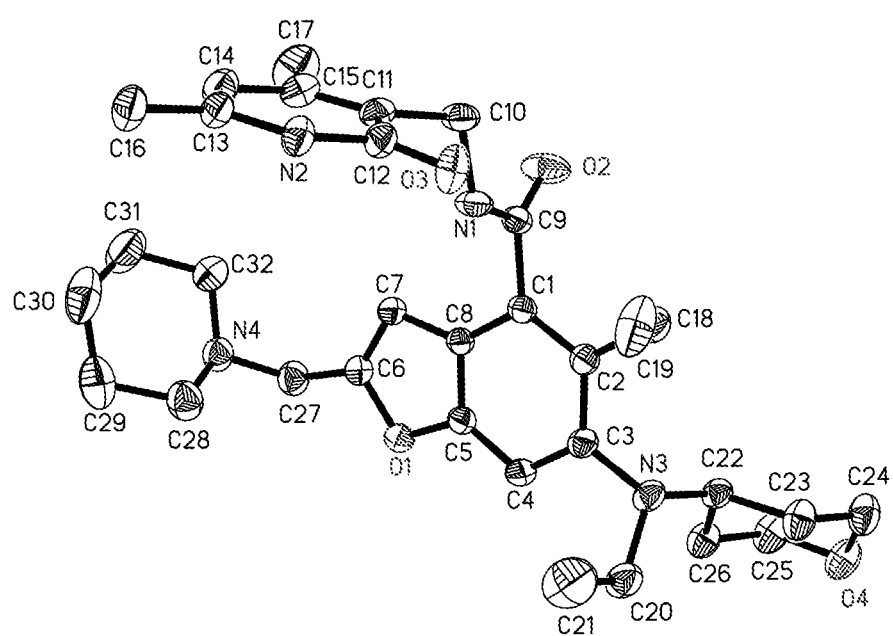
FIG. 16 shows the X-ray single crystal diffraction molecular stereostructure diagram of crystal form D of the compound of formula (I).

The crude product N-((4,6-dimethyl-2-oxo-1,2-dihydropyridin-3 -yl)methyl)-5-ethyl-6-(ethyl(tetrahydro-2 H-pyran-4-yl)amino)-2-(piperidin-1-ylmethyl)benzofuran-4-carboxamide (30mg, 0.055 mmol) obtained in Comparative example 1 was added to a reaction flask, and dissolved in a mixed solvent of methanol and pure water (v/v, 6:1, 1 mL). The mouth of the flask was sealed by a sealing film which was punctured two to three small holes. The solvent was volatilized to obtain a single crystal. The single molecular stereostructure of the crystal sample is shown in FIG. 16 by single crystal X-ray diffraction (XRD), and the unit cell parameters are shown in the following table:

TABLE 6

Unit cell parameters of single crystal of crystal form D

| Parameters | | Values |
|---|---|---|
| Crystal system | | Orthorhombic crystal system |
| Space group | | P bca |
| Unit cell | a (Å) | 17.4737(6) |
| parameters | b (Å) | 17.5933(5) |
| | c (Å) | 19.9907(7) |

TABLE 6-continued

Unit cell parameters of single crystal of crystal form D

| Parameters | Values |
| --- | --- |
| α (°) | 90.0 |
| β (°) | 90.0 |
| γ (°) | 90.0 |
| Unit cell volume V (Å$^3$) | 6145.5(3) |
| Z (Asymmetric unit number in unit cell) | 8 |
| Calculated density (g/cm$^3$) | 1.186 |

EXAMPLE 8

Preparation of Single Crystal of Crystal Form D)

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dissolved in a mixed solvent of ethanol and pure water (v/v, 6:1, 1 mL). The mouth of the flask was sealed by a sealing film which was punctured two to three small holes. The solvent was volatilized to obtain a crystal which was identified as the single crystal of crystal form D by single crystal X-ray diffraction (XRD).

EXAMPLE 9

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and ethyl acetate (300 μL) was added. The mixture was pulped at room temperature for two hours, filtrated and dried to obtain a pale yellow solid, which was identified as crystal form D by XRPD.

EXAMPLE 10

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and propylene glycol methyl ether (300 μL) was added. The mixture was pulped at room temperature for two hours, filtrated and dried to obtain a pale yellow solid, which was identified as crystal form D by XRPD.

EXAMPLE 11

Preparation of Crystal Form D

The crude product N-((4,6-dimethyl-2-oxo-1,2-dihydropyridin-3 -yl)methyl)-5 -ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and cyclohexane (300 μL) was added. The mixture was pulped at 25° C. for two hours, filtrated and dried to obtain a pale yellow solid, which was identified as crystal form D by XRPD.

EXAMPLE 12

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and xylene (300 μL) was added. The mixture was pulped at 25° C. for two hours, filtrated and dried to obtain a pale yellow solid, which was identified as crystal form D by XRPD.

EXAMPLE 13

Preparation of Crystal Form D

The crude product N-((4,6-dimethyl-2-oxo-1,2-dihydropyridin-3 -yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and acetonitrile (300 μL) was added. The mixture was pulped at 50° C. for two hours, filtrated and dried to obtain a pale yellow solid, which was identified as crystal form D by XRPD.

EXAMPLE 14

Preparation of Crystal Form D)

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and acetone (300 μL) was added. The mixture was pulped at 50° C. for two hours, filtrated and dried to obtain a pale yellow solid, which was identified as crystal form D by XRPD.

EXAMPLE 15

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and nitromethane (300 μL) was added. The mixture was pulped at 50° C. for two hours, filtrated and dried to obtain a pale yellow solid, which was identified as crystal form D by XRPD.

EXAMPLE 16

Preparation of crystal form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dimethylformamide (300 μL) was added. The mixture was pulped for two hours, filtrated at 50° C. and dried to obtain a pale yellow solid, which was identified as crystal form D by XRPD.

EXAMPLE 17

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30mg, 0.055 mmol) obtained in Comparative example 1 was added to a reaction flask, and dissolved in isopropanol (1 mL). The solvent was volatilized, and the resulting solid was then dried to obtain a pale yellow solid, which was identified as crystal form D by XRPD.

EXAMPLE 18

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dissolved in a mixed solvent of methanol and water (v/v, 19:1, 300 µL). The solvent was volatilized, and the resulting solid was then filtrated and dried to obtain a pale yellow solid, which was identified as crystal form D by XRPD.

EXAMPLE 19

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dissolved in dioxane (1 mL). The solvent was volatilized, and the resulting solid was then dried to obtain a pale yellow solid, which was identified as crystal form D by XRPD.

EXAMPLE 20

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dissolved in tetrahydrofuran (300 µL). The solution was added with water (900 µL) as an anti-solvent, and the resulting solid was then filtrated and dried to obtain a pale yellow solid, which was identified as crystal form D by XRPD.

EXAMPLE 21

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dimethyl sulfoxide (100 µL) was added. The mixture was pulped at 50° C., filtrated and dried to obtain a pale yellow solid, which was identified as crystal form D by XRPD.

EXAMPLE 22

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and dichloromethane (100 µL) was added. The mixture was pulped at 25° C., filtrated and dried to obtain a pale yellow solid, which was identified as crystal form D by XRPD.

EXAMPLE 23

Preparation of Crystal Form D

The crude product N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide (30 mg, 0.055 mmol) obtained in Comparative example 1 was added to a reaction flask, and methanol (100 µL) was added. The mixture was pulped at 50° C., filtrated and dried to obtain a pale yellow solid, which was identified as crystal form D by XRPD.

EXAMPLE 24.

Study of the Long-Term, Accelerated Stability of Crystal Forms B and D

The sample of crystal form B was spread flat in the air to test sample stability under conditions of 25° C.-65% relative humidity (RH), and the sampling time was Day 20. The sample of crystal form D was spread flat in the air to test sample stability under conditions of 40° C.-75% RH and 25° C.-65% RH, and the sampling time was Day 20.

Figure 10:
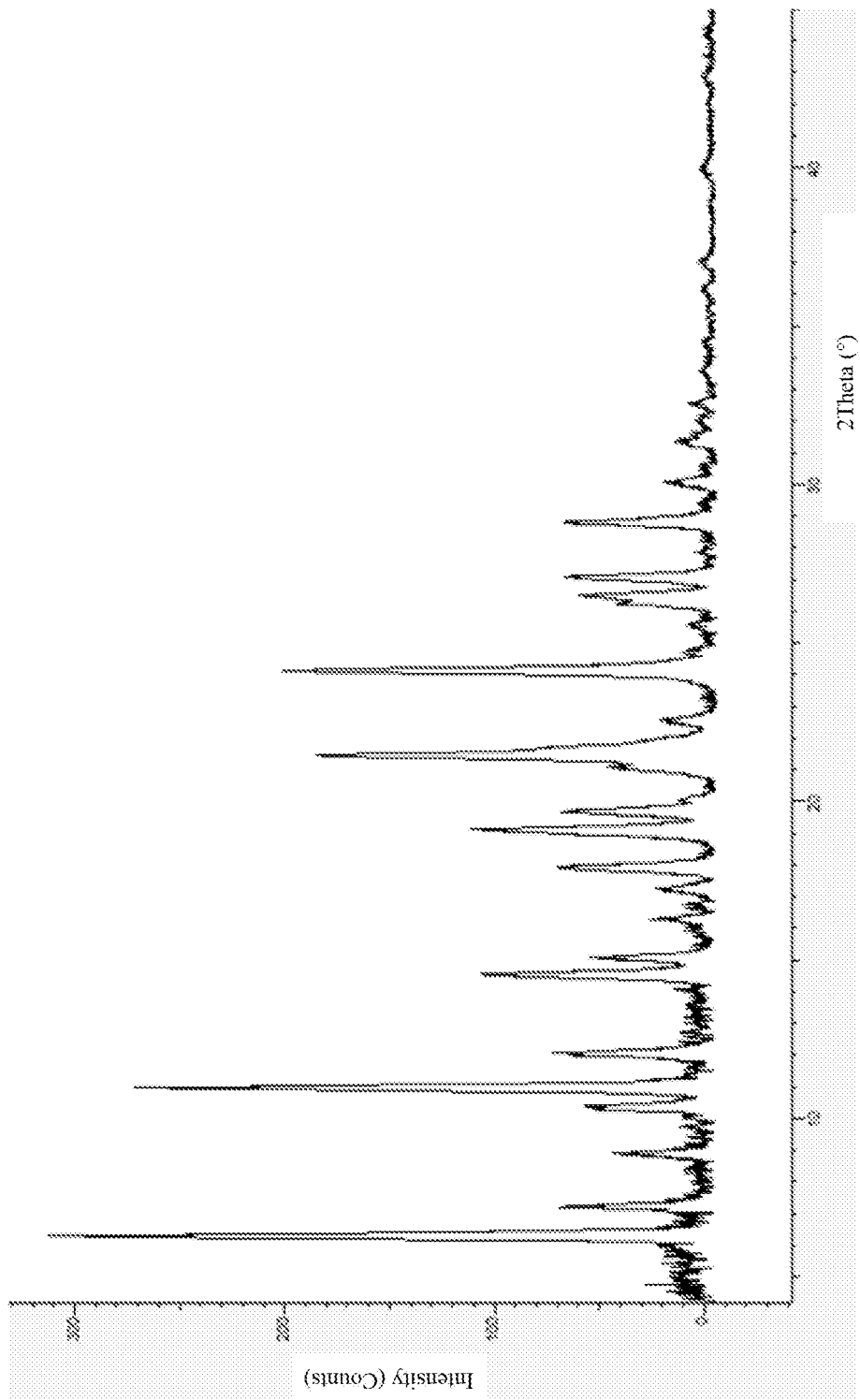
FIG. 10 shows the XRPD spectrum of crystal form B of the compound of formula (I) on Day 0.

Test results:

FIG. 10 shows the XRPD spectrum of crystal form B on Day 0.

Figure 11:
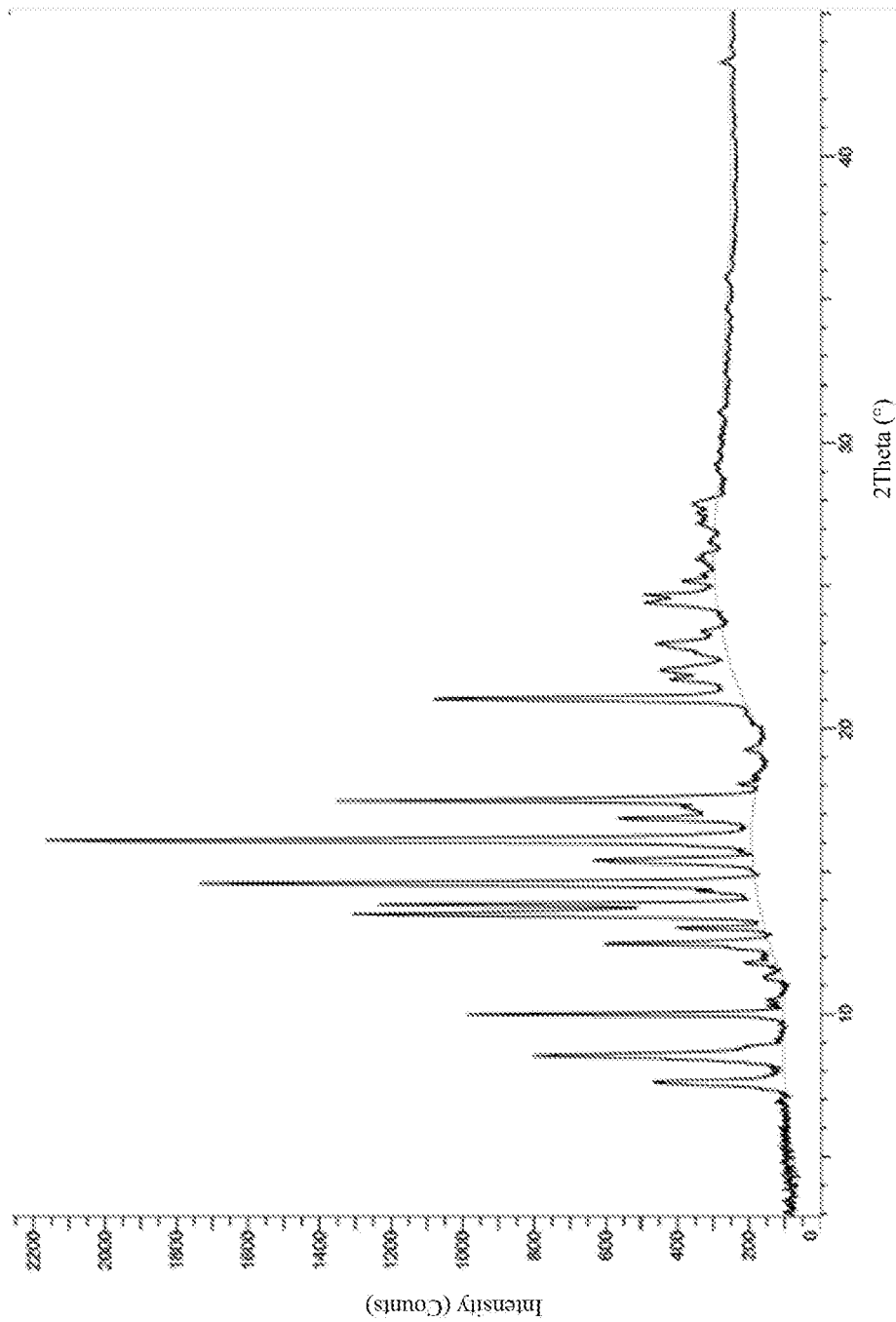
FIG. 11 shows the XRPD spectrum of crystal form B of the compound of formula (I) after 20 days under the conditions of 25° C., RH 65%.

FIG. 11 shows the XRPD spectrum of crystal form B after 20 days under the conditions of 25° C., RH 65% for 20 days.

Figure 12:
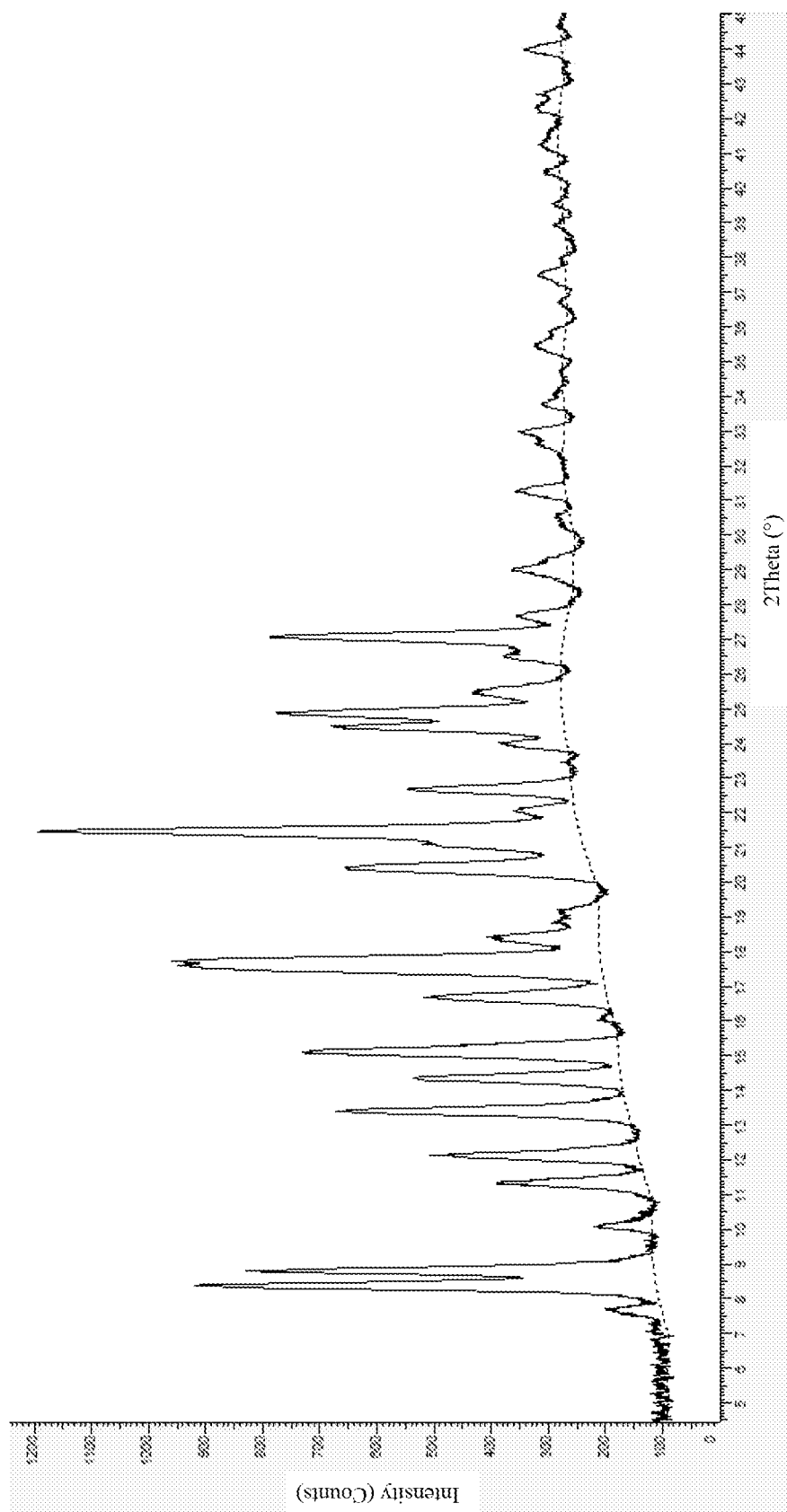
FIG. 12 shows the XRPD spectrum of crystal form D of the compound of formula (I) on Day 0.

FIG. 12 shows the XRPD spectrum of crystal form D on Day 0.

Figure 13:
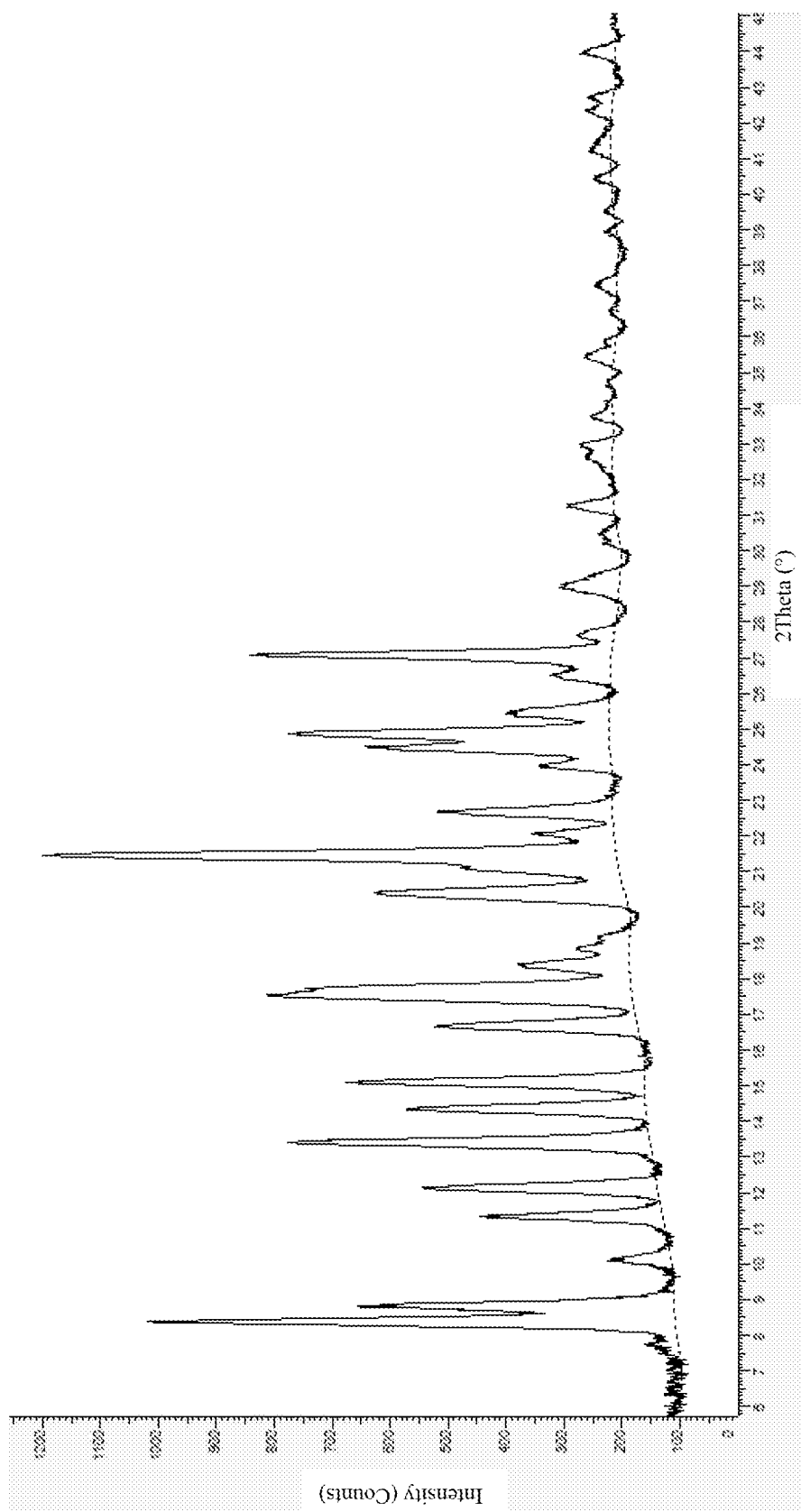
FIG. 13 shows the XRPD spectrum of crystal form D of the compound of formula (I) after 20 days under the conditions of 40° C., RH 75%.

FIG. 13 shows the XRPD spectrum of crystal form D after 20 days under the conditions of 40° C., RH 75% for 20 days.

Figure 14:
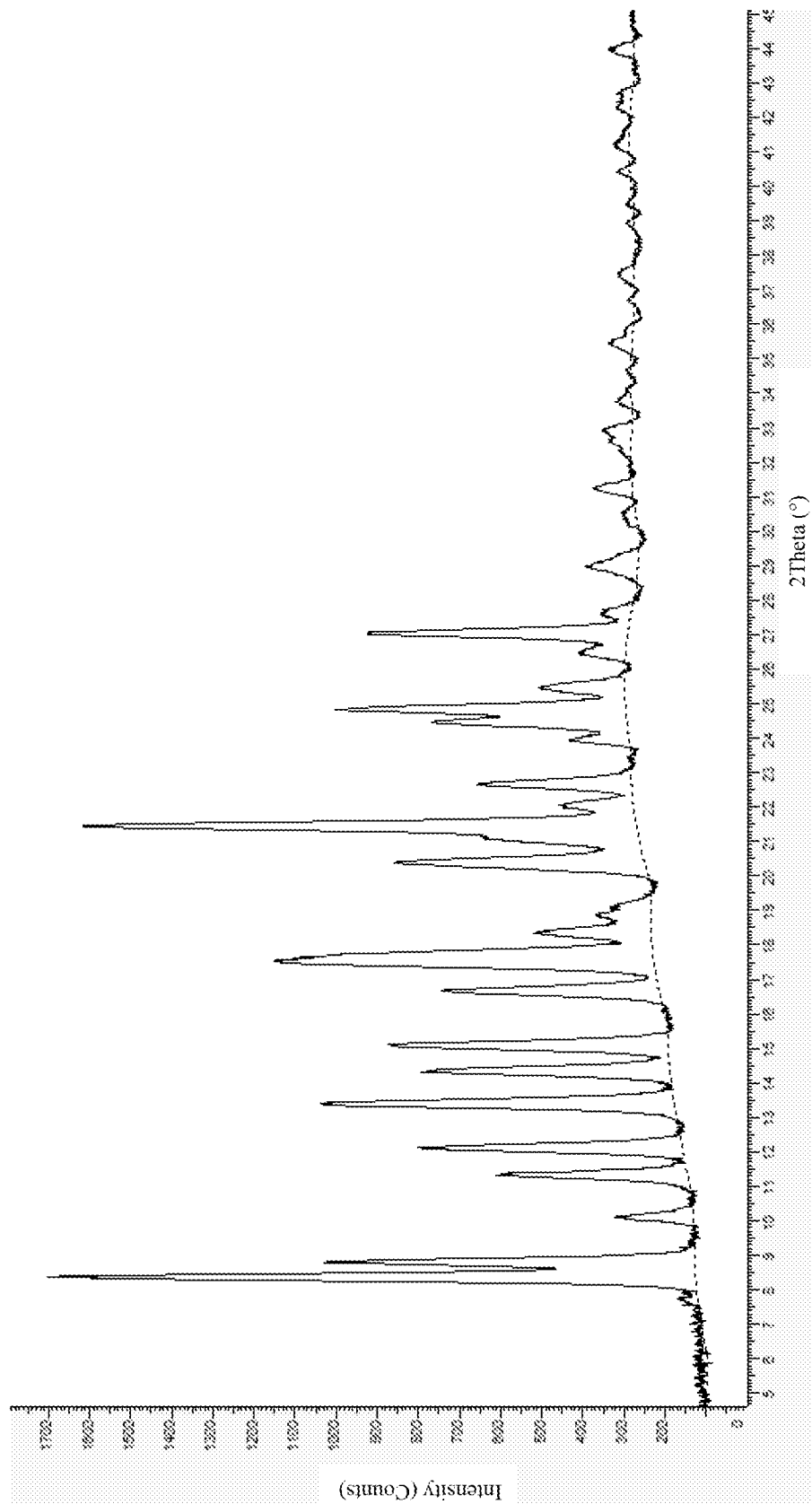
FIG. 14 shows the XRPD spectrum of crystal form D of the compound of formula (I) after 20 days under the conditions of 25° C., RH 65%.

FIG. 14 shows the XRPD spectrum of crystal form D after 20 days under the conditions of 25° C., RH 65% for 20 days.

Test conclusion:

The results of the stability study shown in FIGS. 12, 13 and 14 indicates that the XRPD peaks of the crystal form D of the compound of formula (I) has not changed substantially under the placement conditions of 40° C.-75% RH, and the crystal form is stable. The results shown in FIGS. 10 and 11 indicates that the XRPD peaks of the crystal form B of the compound of formula (I) has changed significantly under the placement conditions of 25° C.-65% RH. It can be seen that the physical stability of crystal form D is better than that of crystal form B under the placement conditions of 25° C.-65%RH.

What is claimed is:

1. A compound of formula (I):

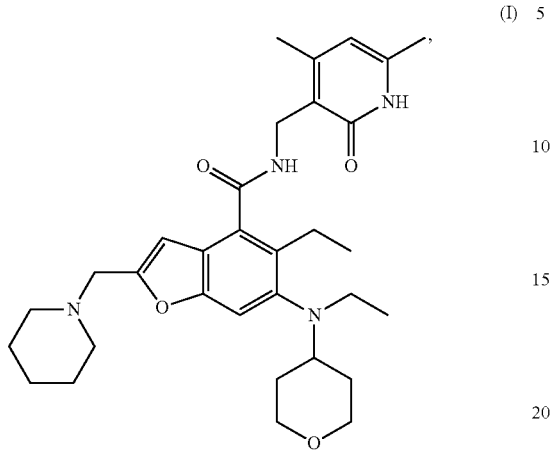

(I)

having a crystal form selected from the group consisting of crystal form A, crystal form B, crystal form C, and crystal form D, wherein:
the crystal form A has a powder X-ray diffraction spectrum comprising characteristic peaks at diffraction angles 2θ±0.2 of 7.60, 8.51, 11.80, 12.38, 13.52, 13.73, 14.48, 15.23, 15.99, 16.10, 16.82, 16.99, 17.35, 18.24, 20.82, 21.57, 21.91, 22.57, 22.76, 22.88, 24.29, 24.47, 25.24, 25.90, 27.23 and 27.74 using Cu-Kα radiation;
the crystal form B has a powder X-ray diffraction spectrum comprising characteristic peaks at diffraction angle 2θ±0.2 of 6.31, 7.24, 10.99, 12.07, 14.56, 17.94, 19.13, 19.71, 21.48, 24.15, 27.10 and 28.83 using Cu-Kα radiation;
the crystal form C has a powder X-ray diffraction spectrum comprising characteristic peaks at diffraction angles 2θ±0.2 of 7.40, 8.62, 9.49, 12.32, 13.39, 15.52, 19.15, 19.17, 21.42 and 22.78 using Cu-Kα radiation; and
the crystal form D has a powder X-ray diffraction spectrum comprising characteristic peaks at diffraction angles 2θ±0.2 of 8.41, 8.85, 11.38, 12.18, 13.45, 15.15, 16.73, 17.59, 17.68, 20.45, 21.51, 22.72, 24.53, 24.91 and 27.11 using Cu-Kα radiation.

2. The compound according to claim 1, wherein the crystal form is crystal form A.

3. The compound according to claim 2, wherein the crystal form A has the powder X-ray diffraction spectrum comprising characteristic peaks at diffraction angles 2θ±0.2 of 7.60, 8.51, 10.37, 11.16, 11.80, 12.38, 12.89, 13.52, 13.73, 14.03, 14.48, 15.23, 15.99, 16.10, 16.43, 16.82, 16.99, 17.35, 18.24, 18.92, 19.17, 20.68, 20.82, 21.57, 21.91, 22.57, 22.76, 22.88, 23.53, 23.68, 24.00, 24.29, 24.47, 24.91, 25.24, 25.72, 25.90, 27.23, 27.74 and 35.63 using Cu-Kα radiation.

4. A method for preparing the compound according to claim 2, selected from the group consisting of:
method I, the method comprising dissolving the compound of formula (I) in a solvent, crystallizing the compound of formula (I) from the solvent using a crystallization method to obtain a crystal, filtering and drying the crystal to obtain the crystal form A, wherein the solvent is selected from the group consisting of an amide solvent, a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile, and the crystallization method is selected from the group consisting of room temperature crystallization, cooling crystallization, solvent volatilization crystallization and crystallization induced by addition of a seed crystal;
method II, the method comprising dissolving the compound of formula (I) in a first solvent to obtain a mixture, adding an anti-solvent to the mixture, crystallizing the compound of formula (I) from the first solvent and anti-solvent using a crystallization method to obtain a crystal, filtering and drying the crystal to obtain the crystal form A, wherein the first solvent is an alcohol solvent selected from the group consisting of methanol and isopropanol, the anti-solvent is water, and the crystallization method is selected from the group consisting of room temperature crystallization, cooling crystallization, solvent volatilization crystallization and crystallization induced by addition of a seed crystal; and
method III, the method comprising adding the compound of formula (I) to a solvent to obtain a mixture, pulping the mixture to obtain a crystal, filtering and drying the crystal to obtain the crystal form A, wherein the solvent is selected from the group consisting of a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile.

5. The compoundcrystal form according to claim 1, wherein the crystal form is crystal form B.

6. The compound according to claim 5, wherein the crystal form B has the powder X-ray diffraction spectrum comprising characteristic peaks at diffraction angles 2θ±0.2 of 6.31, 7.24, 8.92, 10.38, 10.99, 12.07, 14.56, 15.10, 16.36, 17.29, 17.94, 19.13, 19.71, 21.12, 21.48, 22.59, 24.15, 25.45, 26.28, 26.52, 27.10, 28.83, 30.07, 31.37, 32.56, 33.65, 34.64, 36.09, 37.13 and 40.04 using Cu-Kα radiation.

7. A method for preparing the compound according to claim 5, selected from the group consisting of:
method I, the method comprising dissolving the compound of formula (I) in a solvent, crystallizing the compound of formula (I) from the solvent using a crystallization method to obtain a crystal, filtering and drying the crystal to obtain the crystal form B, wherein the solvent is ethanol, and the crystallization method is selected from the group consisting of room temperature crystallization, cooling crystallization, solvent volatilization crystallization and crystallization induced by addition of a seed crystal; and
method II, the method comprising dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form B, wherein the first solvent is ethanol, and the anti-solvent is water, the crystallization method is selected from the group consisting of room temperature crystallization, cooling crystallization, solvent volatilization crystallization and crystallization induced by addition of a seed crystal.

8. The compound according to claim 1, wherein the crystal form is crystal form C.

9. The compound according to claim 8, wherein the crystal form C has the powder X-ray diffraction spectrum comprising characteristic peaks at diffraction angles 2θ±0.2 of 2θ±0.2 of 7.40, 8.62, 9.49, 9.96, 11.12, 12.32, 13.39, 14.21, 14.85, 15.52, 16.50, 17.67, 18.28, 19.15, 19.17, 20.06, 20.80, 21.42, 21.89, 22.20, 22.78, 23.41, 24.74, 25.34, 26.70, 27.38, 28.64, 29.63, 30.20 and 31.15 using Cu-Kα radiation.

10. A method for preparing the compound according to claim 8, the method comprising:

dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form C, wherein the first solvent is an ether solvent, the ether solvent is 1,4-dioxane, the anti-solvent is selected from the group consisting of an aliphatic hydrocarbon solvent and an alicyclic hydrocarbon solvent, and the aliphatic hydrocarbon solvent is n-heptane, the alicyclic hydrocarbon solvent is cyclohexane, and the crystallization method is selected from the group consisting of room temperature crystallization, cooling crystallization, solvent volatilization crystallization and crystallization induced by addition of a seed crystal.

11. The compound according to claim 1, wherein the crystal form is crystal form D.

12. The compound according to claim 11, wherein the crystal form D has the powder X-ray diffraction spectrum comprising characteristic peaks at diffraction angles 2θ±0.2 of 8.41, 8.85, 10.15, 11.38, 12.18, 13.45, 14.40, 15.15, 16.73, 17.59, 17.68, 18.42, 18.91, 19.22, 20.45, 21.15, 21.51, 22.11, 22.72, 24.03, 24.53, 24.91, 25.54, 26.54, 27.11, 27.61, 29.04, 30.49, 31.31, 33.00, 33.88, 35.52, 37.53, 40.46, 41.36, 42.40 and 44.02 using Cu-Kα radiation.

13. A method for preparing the compound according to claim 11, selected from the group consisting of:

method I, the method comprising dissolving the compound of formula (I) in a solvent, crystallizing the compound of formula (I) from the solvent using a crystallization method to obtain a crystal, filtering and drying the crystal to obtain the crystal form D, wherein the solvent is selected from the group consisting of an alcohol solvent, an ether solvent, a mixed solvent of an alcohol and water, a mixed solvent of an ether and water, a mixed solvent of an alcohol and an aliphatic hydrocarbon, and a mixed solvent of an ether and an aliphatic hydrocarbon, the alcohol solvent is selected from the group consisting of methanol, ethanol and isopropanol, the ether solvent is selected from the group consisting of tetrahydrofuran and 1,4-dioxane, and the aliphatic hydrocarbon solvent is n-heptane, and the crystallization method is selected from the group consisting of room temperature crystallization, cooling crystallization, solvent volatilization crystallization and crystallization induced by addition of a seed crystal;

method II, the method comprising dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form D, wherein the first solvent is selected from the group consisting of an alcohol solvent and an ether solvent, the alcohol solvent is selected from the group consisting of methanol and isopropanol, the ether solvent is tetrahydrofuran, and the anti-solvent is water; or the good solvent is an ether solvent, the ether solvent is tetrahydrofuran, the anti-solvent is selected from the group consisting of an aliphatic hydrocarbon solvent and an alicyclic hydrocarbon solvent, the aliphatic hydrocarbon solvent is n-heptane, and the alicyclic hydrocarbon solvent is cyclohexane, and the crystallization method is selected from the group consisting of room temperature crystallization, cooling crystallization, solvent volatilization crystallization and crystallization induced by addition of a seed crystal; and method III, the method comprising adding the compound of formula (I) to a solvent to obtain a mixture, pulping the mixture to obtain a crystal, filtering and drying the crystal to obtain the crystal form D, wherein the solvent is selected from the group consisting of water, an ester, an ether, an aliphatic hydrocarbon, an alicyclic hydrocarbon, a nitroalkane solvent, an arene, an alcohol, a nitrile, a halohydrocarbon, a ketone, a sulfoxide, an amide, a mixed solvent of an alcohol and an ether, a mixed solvent of an alcohol and water, and a mixed solvent of one or more alcohol, the ester solvent is selected from the group consisting of ethyl acetate, isopropyl acetate and butyl acetate, the ether solvent is selected from the group consisting of tetrahydrofuran, 1,4-dioxane, propylene glycol methyl ether and methyl tert-butyl ether, the aliphatic hydrocarbon is n-heptane, the alicyclic hydrocarbon is cyclohexane, the nitroalkane solvent is nitromethane, the arene solvent is selected from the group consisting of xylene and cumene, the alcohol solvent is selected from the group consisting of methanol, ethanol and isopropanol, the nitrile solvent is acetonitrile, the halohydrocarbon solvent is dichloromethane, the ketone solvent is acetone, the sulfoxide is dimethyl sulfoxide, the amide solvent is selected from the group consisting of N,N-dimethylformamide and N,N-dimethylacetamide, the mixed solvent of one or more alcohol is selected from the group consisting of a mixed solvent of methanol and ethanol, a mixed solvent of methanol and isopropanol, and a mixed solvent of ethanol and isopropanol.

14. A pharmaceutical composition comprising the compound according to claim 1 and one or more pharmaceutically acceptable carriers, diluents or excipients.

15. A method for treating a disease associated with EZH2 inhibitor in a subject in need thereof comprising administering to the subject an effective amount of the pharmaceutical composition according to claim 14.

16. The method according to claim 15, wherein the disease associated with EZH2 inhibitor is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma.

17. The method according to claim 16, wherein the leukemia is selected from the group consisting of chronic myeloid leukemia, acute myeloid leukemia and mixed lineage leukemia, and wherein the lymphoma is selected from the group consisting of non-Hodgkin lymphoma, diffuse large B-cell lymphoma and follicular lymphoma.

* * * * *